United States Patent [19]

Tsuji et al.

[11] 4,435,402

[45] Mar. 6, 1984

[54] AMINOPYRIMIDINE DERIVATIVES, PROCESSES FOR THEIR PREPARATION, AND FUNGICIDAL, INSECTICIDAL AND ACARICIDAL COMPOSITIONS CONTAINING THEM

[75] Inventors: Hideakira Tsuji; Shinjiro Yamamoto; Kazuto Nakagami, all of Shiga; Takeo Honda, Ube; Katsutoshi Fujii, Ube; Takashi Kobayashi, Ube; Tokio Obata, Ube; Mikio Kojima, Ube; Yuji Akiyoshi, Ube, all of Japan

[73] Assignees: Sankyo Company, Limited, Tokyo; Ube Industries, Limited, Ube, both of Japan

[21] Appl. No.: 341,776

[22] Filed: Jan. 22, 1982

[30] Foreign Application Priority Data

Jan. 29, 1981 [JP] Japan .................................. 56-11979
Apr. 21, 1981 [JP] Japan .................................. 56-60178

[51] Int. Cl.³ .................... C07D 239/42; A01N 43/54
[52] U.S. Cl. ........................................ 424/251; 71/92; 544/253; 544/326; 544/327; 544/328
[58] Field of Search ............... 544/326, 327, 328, 253; 424/251; 71/92

[56] References Cited

U.S. PATENT DOCUMENTS

| | | | |
|---|---|---|---|
| 2,844,578 | 7/1958 | Acker | 544/327 |
| 3,322,759 | 5/1967 | Carney et al. | 544/253 |
| 3,503,976 | 3/1970 | Reicheneder et al. | 544/326 |
| 3,974,162 | 8/1976 | Santilli et al. | 544/326 |
| 4,213,987 | 7/1980 | Nakagami et al. | 424/251 |
| 4,304,778 | 12/1981 | Nakagami et al. | 424/251 |

FOREIGN PATENT DOCUMENTS 55-76803  4/1980  Japan .................................. 424/251

OTHER PUBLICATIONS

Whitehead et al.; J.A.C.S., vol. 80, pp. 2185–2189, (1958).

*Primary Examiner*—Mary C. Lee
*Attorney, Agent, or Firm*—Frishauf, Holtz, Goodman & Woodward

[57] ABSTRACT

Compounds having the formula (I)

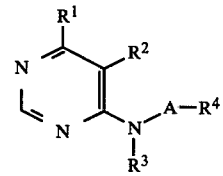

[wherein: $R^1$ and $R^2$ are each alkyl or halogen, or they are trimethylene or tetramethylene; $R^3$ is hydrogen or alkyl; A is alkylene; and $R^4$ is optionally substituted phenyloxy or benzyloxy substituted with at least one alkyl, halogen, alkoxy, alkylthio, alkenyl, trifluoromethyl or nitro; optionally substituted phenyl substituted with one or two halogen atoms, alkyl or alkoxy; furyl or thienyl] and their salts.

53 Claims, No Drawings

AMINOPYRIMIDINE DERIVATIVES, PROCESSES FOR THEIR PREPARATION, AND FUNGICIDAL, INSECTICIDAL AND ACARICIDAL COMPOSITIONS CONTAINING THEM

BACKGROUND OF THE INVENTION

The present invention relates to aminopyrimidine derivatives, to processes for their preparation, and to fungicidal, insecticidal and acaricidal compositions containing them.

Journal of American Chemical Society 80, 2189 (1958) discloses various compounds of use as intermediates for diuretic agents, including, for example, 6-chloro-4-β-phenoxyethylaminopyrimidine, 4-benzylamino-6-chloropyrimidine and 4-furfurylamino-6-chloropyrimidine, but makes no mention of fungicidal, insecticidal or acaricidal activity. Japanese Published Unexamined Patent Application No. 17123/79 (which corresponds to U.S. Pat. No. 4,213,987), 76803/80 and 76804/80 (which corresponds to U.S. Pat. No. 4,304,778) disclose, for instance, 4-(substituted-phenoxyalkylamino)quinazolines as agricultural and horticultural fungicides, insecticides and acaricides.

OBJECTS OF THE INVENTION

It is an object of this invention to provide new aminopyrimidine derivatives which have potent activity against insects, fungi and/or mites and related pests. It is a further object of this invention to provide compositions for agricultural, horticultural, veterinary, or medical use which contain the new aminopyrimidine derivatives. It is a yet further object of this invention to provide processes for producing the potent derivatives of this invention. The invention has as an additional object the salts of the derivatives.

SUMMARY OF THE INVENTION

The present inventors have now discovered that certain aminopyrimidine derivatives substituted in both the 5- and 6-positions of their pyrimidine nucleus with an alkyl group or a halogen atom, and the acid addition salts of such derivatives, are useful as fungicidal, insecticidal and acaricidal agents.

The aminopyrimidine derivatives of this invention are represented by the general formula (I):

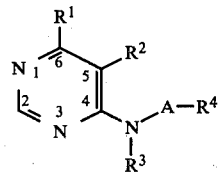

In the formula (I), $R^1$ and $R^2$ are the same or different and are each selected from the group consisting of alkyl groups having from 1 to 6 carbon atoms and halogen atoms, or $R^1$ and $R^2$ jointly represent a trimethylene or tetramethylene group. $R^3$ is selected from the group consisting of a hydrogen atom and alkyl groups having from 1 to 6 carbon atoms. A is an alkylene group. $R^4$ is selected from the group consisting of:

an unsubstituted phenyloxy group,
a substituted phenyloxy group substituted with at least one substituent selected from the group consisting of alkyl groups, halogen atoms, alkoxy groups having from 1 to 6 carbon atoms, alkylthio groups having from 1 to 6 carbon atoms, alkenyl groups having from 2 to 6 carbon atoms, a trifluoromethyl group and a nitro group,
an unsubstituted benzyloxy,
a substituted benzyloxy group substituted in the phenyl ring with at least one substituent selected from the group consisting of alkyl groups, halogen atoms, alkoxy groups having from 1 to 6 carbon atoms, alkylthio groups having from 1 to 6 carbon atoms, alkenyl groups having from 2 to 6 carbon atoms, a trifluoromethyl group and a nitro group,
an unsubstituted phenyl group,
a substituted phenyl group substituted with one or two substituents selected from the group consisting of halogen atoms, alkyl groups having from 1 to 6 carbon atoms and alkoxy groups having from 1 to 6 carbon atoms,
a furyl group, and
a thienyl group.

DESCRIPTION OF THE INVENTION

Where $R^1$ and $R^2$ represent alkyl groups having from 1 to 6 carbon atoms, they may be for example straight or branched chain alkyl groups having from 1 to 4 carbon atoms, such as a methyl, ethyl, n-propyl, isopropyl or n-butyl group, particularly a methyl or ethyl group, more particularly a methyl group.

Where $R^1$ and $R^2$ represent halogen atoms, they may be for example a chlorine or bromine atom.

Where $R^3$ represents an alkyl group having from 1 to 6 carbon atoms, it may be one of the alkyl groups illustrated for $R^1$ and $R^2$, for example a methyl group. However $R^3$ is preferably a hydrogen atom.

The group A may for example represent a straight or branched chain alkylene group having from 1 to 5 carbon atoms, such as a methylene, ethylene, methylmethylene (ethylidene), trimethylene, ethylmethylene (propylidene), dimethylmethylene, propylene, tetramethylene, 1,1-, 1,2- or 2,2-dimethylethylene, 1- or 2-ethylethylene or pentamethylene group, particularly an alkylene group having from 2 to 5 carbon atoms, more particularly an ethylene group or a group of the formula —CH($R^8$)— where $R^8$ is an alkyl group having from 1 to 4 carbon atoms especially a methyl or ethyl group.

In one aspect of the present invention, the group $R^4$ is a group —$OR^5$ which is one of the unsubstituted phenyloxy, substituted phenyloxy, unsubstituted benzyloxy, or substituted benzyloxy groups. The compounds are then of the formula (II)

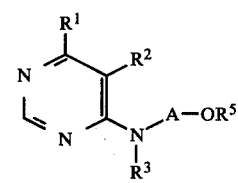

wherein $R^1$, $R^2$, $R^3$ and A are as defined and $R^5$ is correspondingly an optionally substituted phenyl or benzyl group.

Where $R^5$ is substituted in the phenyl ring, there will usually be from one to three substituents selected from alkyl groups, halogen atoms, alkoxy groups having from 1 to 6 carbon atoms, alkylthio groups having from 1 to 6 carbon atoms, alkenyl groups having from 2 to 6 carbon atoms, a trifluoromethyl group and a nitro group. Suitable alkyl groups include, for example, straight or branched chain alkyl groups having from 1 to 10 carbon atoms, such as a methyl, ethyl, n-propyl, isopropyl, n-butyl, isobutyl, sec or t-butyl, n-pentyl, isopentyl, 2-ethylpropyl, 2,2-dimethylpropyl, n-hexyl, 2-ethylbutyl, n-heptyl, n-octyl, 2-ethylhexyl, nonyl or decyl group; suitable halogens include, for example, a chlorine, bromine, fluorine or iodine atom; suitable alkoxy groups include, for example, straight or branched chain alkoxy groups having from 1 to 4 carbon atoms, such as a methoxy, ethoxy, n-propoxy, isopropoxy or n-butoxy group; suitable alkylthio groups include, for example, straight or branched chain alkylthio groups having from 1 to 4 carbon atoms, such as a methylthio or ethylthio group; and suitable alkenyl groups include, for example, an allyl, methallyl or 2-butenyl group.

Preferred compounds of the formula (II) comprise those wherein $R^1$ and $R^2$ are each alkyl groups having from 1 to 4 carbon atoms or halogen atoms, or $R^1$ and $R^2$ jointly represent a trimethylene or tetramethylene group; $R^3$ is hydrogen atom or an alkyl group having from 1 to 4 carbon atoms, especially a hydrogen atom; A is an alkylene group having from 1 to 5 carbon atoms, especially an alkylene group having from 2 to 4 carbon atoms and more especially an ethylene group; and $R^5$ is unsubstituted phenyl group or a substituted phenyl group substituted with one, two or three substituents selected from alkyl groups having from 1 to 10 carbon atoms, halogen atoms, alkoxy groups having from 1 to 4 carbon atoms, alkylthio groups having from 1 to 4 carbon atoms, alkenyl groups having from 3 to 4 carbon atoms, a trifluoromethyl group and a nitro group.

Especially preferred compounds of formula (II) are those wherein $R^1$ and $R^2$ are each methyl groups, or one of $R^1$ and $R^2$ is an alkyl group having from 1 to 4 carbon atoms, especially a methyl group, and the other is a chlorine or bromine atom.

$R^5$ is the preferred compounds of formula (II) is suitably selected from a substituted phenyl group substituted with one or two alkyl groups having from 1 to 10 carbon atoms or with one alkyl group having from 1 to 10 carbon atoms and with one alkyl group, especially a phenyl group substituted at the 2-position with an alkyl group having from 1 to 4 carbon atoms or a phenyl group substituted at the 2-position with a methyl or ethyl group and at the 4- or 5-position with an alkyl group having from 1 to 10 carbon atoms or with an allyl group; or a phenyl group substituted at the 2-position with a methyl group, at the 4- or 5-position with an alkyl group having from 1 to 10 carbon atoms and at the 6-position with a methyl group or halogen atom.

In the compounds (II) wherein $R^1$ is an alkyl group having from 1 to 4 carbon atoms and $R^2$ is a chlorine or bromine atom, it is preferred that $R^3$ is a hydrogen atom; A is an ethylene group; and $R^5$ is a phenyl group substituted at the 2-position with an alkyl group having from 1 to 4 carbon atoms; a phenyl group substituted at the 2-position with a methyl or ethyl group and at the 4- or 5-position with an alkyl group having from 1 to 10 carbon atoms or with an allyl group; or a phenyl group substituted at the 2-position with a methyl group, at the 4-position with an alkyl group having from 1 to 10 carbon atoms and at the 6-position with a methyl group or a halogen atom.

In particular, for preferred compounds of formula (II), $R^1$ is a methyl group; $R^2$ is a chlorine or bromine atom; $R^3$ is a hydrogen atom; A is an ethylene group; and $R^5$ is a phenyl group substituted at the 2-position with a methyl group and at the 4-position with an n-alkyl group having from 2 to 8 carbon atoms.

In another aspect of the present invention, the group $R^4$ is a group $R^6$ which is one of the unsubstituted phenyl, substituted phenyl group, furyl and thienyl groups. The compounds are then of the formula (III)

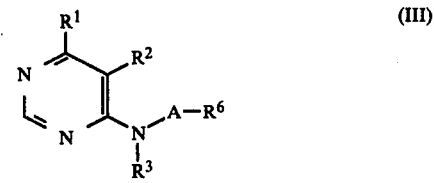

wherein $R^1$, $R^2$, $R^3$ and A are as defined and $R^6$ is correspondingly an optionally substituted phenyl group, a furyl group or a thienyl group.

Where $R^6$ is a substituted phenyl group, there will be one or two substituents selected from halogen atoms (for instance a chlorine, bromine, fluorine or iodine atom); alkyl groups, for example, a straight or branched chain alkyl group having from 1 to 5 carbon atoms (for instance a methyl, ethyl, n-propyl, isopropyl, n-butyl or n-pentyl group); and alkoxy groups, for example an alkoxy group having from 1 to 4 carbon atoms (for instance a methoxy, ethoxy, n-propoxy, isopropoxy or n-butoxy group).

Preferred compounds of the formula (III) comprise those wherein $R^1$ and $R^2$ are each alkyl groups having from 1 to 4 carbon atoms or halogen atoms; $R^3$ is a hydrogen atom; A is an alkylene group having from 1 to 5 carbon atoms, especially a group of formula —CH($R^8$)— in which $R^8$ is an alkyl group having from 1 to 4 carbon atoms such as a methyl or ethyl group; and $R^6$ is unsubstituted phenyl group, a substituted phenyl group substituted with one or two substituents selected from halogen atoms, alkyl groups having from 1 to 5 carbon atoms, and alkoxy groups having from 1 to 4 carbon atoms, a furyl group or a thienyl group.

Particularly preferred compounds of formula (III) are those wherein one of $R^1$ and $R^2$ is a chlorine or bromine atom and the other is an alkyl group having from 1 to 4 carbon atoms.

$R^6$ is suitably selected from an unsubstituted phenyl group or a substituted phenyl group substituted with one substituent selected from alkyl groups having from 1 to 4 carbon atoms, especially a methyl group, alkoxy groups having from 1 to 4 carbon atoms, especially a methoxy group, and halogen atoms, especially a chlorine or bromine atom.

In particularly preferred compounds of formula (III), $R^1$ is a chlorine or bromine atom; $R^2$ is a methyl or ethyl group; $R^3$ is a hydrogen atom; A is an ethylene or propylene group; and $R^6$ is a phenyl group or a phenyl group substituted with one methyl or methoxy group.

In the compounds of formula (I), there is the possibility of optical isomerism, particularly when the alkylene group A contains one or more asymmetric carbon atoms. The present invention includes the individual optical isomers, as well as racemic mixtures.

Compounds of the formula (I) readily form acid addition salts, which are also included within the scope of the invention. Acids for formation of such acid addition salts include inorganic acids, for example hydrochloric acid, hydrobromic acid, nitric acid, sulphuric acid or phosphoric acid; carboxylic acids, for example, formic acid, oxalic acid or trichloroacetic acid; and organic sulphonic acids, for example, methanesulphonic acid or benzenesulphonic acid. Of these salts, a hydrochloride is preferred.

Representative compounds of formula (I) are listed below with each compound being given a number for subsequent ease of reference. Where a melting point is quoted the values are in degrees Celsius, where an optical rotation is quoted the value is for the $Na_D$ line, and where a refractive index n is quoted the value is for the $Na_D$ line: such compounds were prepared using the process of the invention described below.

1. 5,6-dimethyl-4-(2-phenoxyethylamino)pyrimidine mp 99–101
2. 5,6-dimethyl-4-[2-(2-methylphenoxy)ethylamino]pyrimidine mp 107–109
3. 5,6-dimethyl-4-[2-(2-ethylphenoxy)ethylamino]pyrimidine mp 76–78
4. 5,6-dimethyl-4-[2-(2-n-propylphenoxy)ethylamino]pyrimidine mp 71–72
5. 5,6-dimethyl-4-[2-(2-isopropylphenoxy)ethylamino]pyrimidine mp 71–73
6. 4-[2-(2-sec-butylphenoxy)ethylamino]-5,6-dimethylpyrimidine mp 70–72
7. 4-[2-(2-t-butylphenoxy)ethylamino]-5,6-dimethylpyrimidine mp 87–89
8. 4-[2-(allylphenoxy)ethylamino]-5,6-dimethylpyrimidine mp 73–75
9. 4-[2-(chlorophenoxy)ethylamino]-5,6-dimethylpyrimidine mp 112–114
10. 5,6-dimethyl-4-[2-(4-methylphenoxy)ethylamino]pyrimidine mp 103–105
11. 5,6-dimethyl-4-[2-(2,4-dimethylphenoxy)ethylamino]pyrimidine mp 88–90
12. 5,6-dimethyl-4-[2-(4-ethyl-2-methylphenoxy)ethylamino]pyrimidine mp 60–63
13. 5,6-dimethyl-4-[2-(2-methyl-4-n-propylphenoxy)ethylamino]pyrimidine mp 71–73
14. 5,6-dimethyl-4-[2-(2-methyl-4-isopropylphenoxy)ethylamino]pyrimidine mp 97–99
15. 4-[2-(4-n-butyl-2-methylphenoxy)ethylamino)-5,6-dimethylpyrimidine mp 64–67
16. 5,6-dimethyl-4-[2-(2-methyl-4-n-pentylphenoxy)ethylamino]pyrimidine mp 85–87
17. 5,6-dimethyl-4-[2-(2-methyl-4-isopropylphenoxy)ethylamino]pyrimidine mp 80–81
18. 5,6-dimethyl-4-[2-(4-n-hexyl-2-methylphenoxy)ethylamino]pyrimidine hydrochloride mp 96–99
19. 5,6-dimethyl-4-[2-(4-n-heptyl-2-methylphenoxy)ethylamino]pyrimidine mp 75–77
20. 5,6-dimethyl-4-[2-(2-methyl-4-n-octylphenoxy)ethylamino]pyrimidine hydrochloride mp 120–123
21. 5,6-dimethyl-4-[2-(2-methyl-4-n-nonylphenoxy)ethylamino]pyrimidine mp 76–78
22. 4-[2-(4-n-decyl-2-methylphenoxy)ethylamino)-5,6-dimethylpyrimidine mp 64–66
23. 4-[2-(2-n-butyl-4-methylphenoxy)ethylamino]-5,6-dimethylpyrimidine mp 51–55
24. 4-[2-(4-chloro-2-methylphenoxy)ethylamino]-5,6-dimethylpyrimidine mp 99–101
25. 5,6-dimethyl-4-[2-(2-methyl-5-isopropylphenoxy)ethylamino]pyrimidine $n_D^{20}$ 1.5606
26. 5-ethyl-6-methyl-4-[2-(2-methyl-4-n-propylphenoxy)ethylamino]pyrimidine mp 72–74
27. 4-[2-(4-n-butyl-2-methylphenoxy)ethylamino]-5-ethyl-6-methylpyrimidine mp 62–64
28. 5-ethyl-6-methyl-4-[2-(2-methyl-4-n-pentylphenoxy)ethylamino]pyrimidine mp 79–81
29. 5-ethyl-4-[2-(4-n-heptyl-2-methylphenoxy)ethylamino]-6-methylpyrimidine mp 70–71
30. 4-[2-(4-n-butyl-2-methylphenoxy)ethylamino]-6-methyl-5-n-propylpyrimidine mp 58–60
31. 5-n-butyl-6-methyl-4-[2-(2-methylphenoxy)ethylamino]pyrimidine mp 92–94
32. 5-n-butyl-4-[2-(2-ethylphenoxy)ethylamino)-6-methylpyrimidine mp 70–72
33. 5-n-butyl-6-methyl-4-[2-(2-methyl-4-n-propylphenoxy)ethylamino]pyrimidine mp 46–48
34. 5-n-butyl-6-methyl-4-[2-(2-methyl-4-n-pentylphenoxy)ethylamino]pyrimidine mp 78–80
35. 5-n-butyl-4-[2-(4-n-heptyl-2-methylphenoxy)ethylamino]-6-methyl-pyrimidine mp 62–64
36. 5-n-butyl-6-methyl-4-[2-(2-methyl-5-isopropylphenoxy)ethylamino]pyrimidine $n_D^{23}$ 1.5472
37. 5-bromo-6-chloro-4-[2-(2,4-dimethylphenoxy)ethylamino]pyrimidine mp 70–72
38. 5-chloro-6-methyl-4-(2-phenoxyethylamino)pyrimidine mp 83–85
39. 5-chloro-6-methyl-4-[2-(methyl-2-phenoxy)ethylamino]pyrimidine mp 68–70
40. 5-chloro-4-[2-(2-ethylphenoxy)ethylamino]-6-methylpyrimidine $n_D^{21}$ 1.5758
41. 5-chloro-6-methyl-4-[2-(2-n-propylphenoxy)ethylamino]pyrimidine $n_D^{21}$ 1.5620
42. 5-chloro-6-methyl-4-[2-(2-isopropylphenoxy)ethylamino]pyrimidine $n_D^{21}$ 1.5679
43. 4-[2-(2-sec-butylphenoxy)ethylamino]-5-chloro-6-methylpyrimidine $n_D^{21}$ 1.5635
44. 4-[2-(2-t-butylphenoxy)ethylamino]-5-chloro-6-methylpyrimidine $n_D^{20}$ 1.5640
45. 4-[2-(2-allylphenoxy)ethylamino]-5-chloro-6-methylpyrimidine $n_D^{21}$ 1.5793
46. 5-chloro-4-[2-(2-chlorophenoxy)ethylamino]-6-methylpyrimidine mp 85–87
47. 5-chloro-6-methyl-4-[2-(4-methylphenoxy)ethylamino]pyrimidine mp 84–86
48. 5-chloro-4-[2-(2,4-dimethylphenoxy)ethylamino]-6-methylpyrimidine mp 67–69
49. 5-chloro-4-[2-(4-ethyl-2-methylphenoxy)ethylamino]-6-methylpyrimidine mp 85–87
50. 5-chloro-6-methyl-4-[2-(2-methyl-4-n-propylphenoxy)ethylamino]pyrimidine $n_D^{20}$ 1.5539
51. 5-chloro-6-methyl-4-[2-(2-methyl-4-isopropylphenoxy)ethylamino]pyrimidine $n_D^{18}$ 1.5633
52. 4-[2-(4-n-butyl-2-methylphenoxy)ethylamino]-5-chloro-6-methylpyrimidine $n_D^{26}$ 1.5470
53. 4-[2-(4-isobutyl-2-methylphenoxy)ethylamino]-5-chloro-6-methylpyrimidine $n_D^{23}$ 1.5561
54. 5-chloro-6-methyl-4-[2-(2-methyl-4-n-pentylphenoxy)ethylamino]pyrimidine $n_D^{25}$ 1.5530
55. 5-chloro-6-methyl-4-[2-(2-methyl-4-isopentylphenoxy)ethylamino]pyrimidine $n_D^{26}$ 1.5490
56. 5-chloro-6-methyl-4-{2-[2-methyl-4-(2-methylbutyl)phenoxy]ethylamino}pyrimidine $n_D^{22.6}$ 1.5450
57. 5-chloro-6-methyl-4-[2-(2-methyl-4-neopentylphenoxy)ethylamino]pyrimidine $n_D^{23}$ 1.5600
58. 5-chloro-4-[2-(4-n-hexyl-2-methylphenoxy)ethylamino]-6-methylpyrimidine $n_D^{25}$ 1.5505
59. 5-chloro-4-{2-[4-(2-ethylbutyl)-2-methylphenoxy]ethylamino}-6-methyl-pyrimidine $n_D^{23.4}$ 1.5415
60. 5-chloro-4-[2-(4-n-heptyl-2-methylphenoxy)ethylamino]-6-methylpyrimidine $n_D^{18}$ 1.5448

61. 5-chloro-6-methyl-4-[2-[2-methyl-4-n-octyl-phenoxy)ethylamino]pyrimidine $n_D^{25}$ 1.5428
62. 5-chloro-4-{2-[4-(2-ethylhexyl)-2-methylphenoxy]ethylamino}-6-methylpyrimidine $n_D^{23}$ 1.5464
63. 5-chloro-6-methyl-4-[2-(2-methyl-4-n-nonyl-phenoxy)ethylamino]pyrimidine mp 44–46
64. 5-chloro-6-methyl-4-{2-[2-methyl-4-(3,5,5-trimethylhexyl)phenoxy]ethylamino}pyrimidine $n_D^{23.5}$ 1.5404
65. 5-chloro-4-[2-(4-decyl-2-methylphenoxy)ethamino]-6-methylpyrimidine mp 42–45
66. 5-chloro-4-[2-(4-chloro-2-methylphenoxy)ethylamino]-6-methylpyrimidine mp 78–79
67. 5-chloro-6-methyl-4-[2-(2-methyl-5-isopropyl-phenoxy)ethylamino]pyrimidine $n_D^{21}$ 1.5650
68. 5-chloro-4-[2-(2,4-dimethylphenoxy)ethylamino]-6-n-propylpyrimidine $n_D^{22}$ 1.5650
69. 5-chloro-4-[2-(2-methyl-4-n-propylphenoxy)ethylamino]-6-n-propylpyrimidine $n_D^{21}$ 1.5562
70. 4-[2-(4-n-butyl-2-methylphenoxy)ethylamino]-5-chloro-6-n-propylpyrimidine $n_D^{21}$ 1.5502
71. 5-chloro-4-[2-(2-methyl-4-n-pentylphenoxy)ethylamino]-6-n-propylpyrimidine $n_D^{21}$ 1.5469
72. 5-chloro-4-[2-(4-chloro-2-methylphenoxy)ethylamino]-6-n-propylpyrimidine $n_D^{22}$ 1.5737
73. 4-[2-(2-n-butyl-6-methylphenoxy)ethylamino]-5-chloro-6-methylpyrimidine $n_D^{21}$ 1.5568
74. 5-chloro-6-methyl-4-[2-(2-methyl-6-n-pentyl-phenoxy)ethylamino]yrimidine $n_D^{21}$ 1.5572
75. 5-chloro-4-[2-(2-n-hexyl-6-methylphenoxy)ethylamino]-6-methylpyrimidine $n_D^{21}$ 1.5490
76. 5-chloro-6-methyl-4-[2-(2-methyl-6-n-octyl-phenoxy)ethylamino]pyrimidine $n_D^{21}$ 1.5429
77. 5-bromo-6-methyl-4-(2-phenoxyethylamino)-pyrimidine mp 68–70
78. 5-chloro-6-methyl-4-[2-(2-methylphenoxy]ethylamino]pyrimidine mp 77–79
79. 5-bromo-4-[2-(2-ethylphenoxy)ethylamino]-6-methylpyrimidine $n_D^{21}$ 1.5900
80. 5-bromo-6-methyl-4-[2-(2-n-propylphenoxy)ethylamino]pyrimidine $n_D^{22}$ 1.5705
81. 5-bromo-6-methyl-4-[2-(2-isopropylphenoxy)ethylamino]pyrimidine $n_D^{21}$ 1.5777
82. 4-[2-(2-sec-butylphenoxy)ethylamino]-5-bromo-6-methylpyrimidine $n_D^{22}$ 1.5742
83. 5-bromo-4-[2-(2-butylphenoxy)ethylamino]-6-methylpyrimidine $n_D^{22}$ 1.5770
84. 4-[2-(2-allylphenoxy)ethylamino]-5-bromo-6-methylpyrimidine $n_D^{22}$ 1.5901
85. 5-bromo-4-[2-(2,4-dimethylphenoxy)ethylamino]-6-methylpyrimidine mp 72–74
86. 5-bromo-4-[2-(4-ethyl-2-methylphenoxy)ethylamino]-6-methylpyrimidine mp 66–68
87. 5-bromo-6-methyl-4-[2-(2-methyl-4-n-propyl-phenoxy)ethylamino]pyrimidine $n_D^{26}$ 1.5658
88. 5-bromo-6-methyl-4-[2-(2-methyl-4-isopropyl-phenoxy)ethylamino]pyrimidine $n_D^{27.5}$ 1.5664
89. 5-bromo-4-[2-(4-n-butyl-2-methylphenoxy)ethylamino]-6-methylpyrimidine $n_D^{26}$ 1.5599
90. 5-bromo-4-[2-(4-isobutyl-2-methylphenoxy)ethylamino]-6-methylpyrimidine $n_D^{23.5}$ 1.5688
91. 5-bromo-6-methyl-4-[2-(2-methyl-4-n-pentyl-phenoxy)ethylamino]pyrimidine $n_D^{26}$ 1.5520
92. 5-bromo-6-methyl-4-[2-(2-methyl-4-isopentyl-phenoxy)ethylamino]pyrimidine $n_D^{26}$ 1.5539
93. 5-bromo-6-methyl-4-{2-[2-methyl-4-(2-methylbutyl)phenoxy]ethylamino}pyrimidine $n_D^{23.6}$ 1.5604
94. 5-bromo-6-methyl-4-[2-(2-methyl-4-neopentyl-phenoxy)ethylamino]pyrimidine $n_D^{24}$ 1.5708
95. 5-bromo-4-[2-(4-n-hexyl-2-methylphenoxy)ethylamino]-6-methylpyrimidine $n_D^{26}$ 1.5509
96. 5-bromo-4-{2-[4-(2-ethylbutyl)-2-methylphenoxy]ethylamino}-6-methylpyrimidine $n_D^{23.1}$ 1.5584
97. 5-bromo-4-[2-(4-n-heptyl-2-methylphenoxy)ethylamino]-6-methylpyrimidine $n_D^{26}$ 1.5478
98. 5-bromo-6-methyl-4-[2-(2-methyl-4-n-octyl-phenoxy)ethylamino]pyrimidine $n_D^{26}$ 1.5450
99. 5-bromo-4-{2-[4-(2-ethylhexyl)-2-methylphenoxy]ethylamino}-6-methylpyrimidine $n_D^{22.7}$ 1.5550
100. 5-bromo-6-methyl-4-[2-(2-methyl-4-n-nonyl-phenoxy)ethylamino]pyrimidine $n_D^{26}$ 1.5390
101. 5-bromo-4-{2-[2-methyl-4-(3,5,5-trimethylhexyl)phenoxy]ethylamino}-6-methylpyrimidine $n_D^{23}$ 1.5489
102. 5-bromo-4-[2-(4-n-decyl-2-methylphenoxy)ethylamino]-6-methylpyrimidine mp 43–45
103. 5-bromo-4-[2-(4-chloro-2-methylphenoxy)ethylamino]-6-methylpyrimidine mp 91–93
104. 5-bromo-6-methyl-4-[2-(2-methyl-5-isopropyl-phenoxy)ethylamino]pyrimidine $n_D^{21}$ 1.5745
105. 5-bromo-4-[2-(2,4-dimethylphenoxy)ethylamino]-6-n-propylpyrimidine mp 56–57
106. 5-bromo-4-[2-(2-methyl-4-n-propylphenoxy)ethylamino]-6-n-propypyrimidine $n_D^{23}$ 1.5630
107. 5-bromo-4-[2-(4-n-butyl-2-methyl-phenoxy)ethylamino]-6-n-propylpyrimidine $n_D^{23}$ 1.5570
108. 5-bromo-4-[2-(2-methyl-4-n-pentylphenoxy)ethylamino]-6-n-propylpyrimidine $n_D^{23}$ 1.5550
109. 5-bromo-4-[2-(4-chloro-2-methylphenoxy)ethylamino]-6-n-propylpyrimidine mp 42–45
110. 6-chloro-5-methyl-4-[2-(2-methylphenoxy)ethylamino]pyrimidine mp 115–116
111. 6-chloro-4-[2-(2-ethylphenoxy)ethylamino]-5-methylpyrimidine mp 93–95
112. 6-chloro-5-methyl-4-[2-(2-n-propylphenoxy)ethylamino]pyrimidine mp 62–65
113. 6-chloro-5-methyl-4-[2-(2-isopropylphenoxy)ethylamino]pyrimidine mp 65–67
114. 4-[2-(2-sec-butylphenoxy)ethylamino]-6-chloro-5-methylpyrimidine mp 63–65
115. 4-[2-(2-t-butylphenoxy)ethylamino]-6-chloro-5-methylpyrimidine mp 93–95
116. 4-[2-(2-allylphenoxy)ethylamino]-6-chloro-5-methylpyrimidine mp 75–77
117. 6-chloro-4-[2-(2-iodophenoxy)ethylamino]-5-methylpyrimidine mp 123–124
118. 6-chloro-4-[2-(2-methoxyphenoxy)ethylamino]-5-methylpyrimidine mp 127–129
119. 6-chloro-5-methyl-4-[2-(2-trifluoromethylylphenoxy)ethylamino]pyrimidine mp 104–106
120. 6-chloro-4-[2-(4-fluorophenoxy)ethylamino]-5-methylpyrimidine mp 153–155
121. 6-chloro-4-[2-(3-chloro-2-methylphenoxy)ethylamino]-5-methylpyrimidine mp 127–130
122. 6-chloro-5-methyl-4-[2-(2-methyl-5-isopropyl-phenoxy)ethylamino]pyrimidine $n_D^{24}$ 1.5633
123. 6-chloro-5-methyl-4-[2-(2-methyl-6-n-propyl-phenoxy)ethylamino]pyrimidine mp 84–86
124. 6-chloro-5-methyl-4-[2-(3-methyl-4-methylthio-phenoxy)ethylamino]pyrimidine mp 140–143
125. 6-chloro-5-methyl-4-[2-(2,4-dimethylphenoxy)ethylamino]pyrimidine mp 70–72
126. 6-chloro-4-[2-(4-ethyl-2-methylphenoxy)ethylamino]-5-methylpyrimidine mp 68–70

127 6-chloro-5-methyl-4-[2-(2-methyl-4-n-propylphenoxy)ethylamino]pyrimidine mp 47–49
128 6-chloro-5-methyl-4-[2-(2-methyl-4-isopropylphenoxy)ethylamino]pyrimidine $n_D^{26}$ 1.5658
129 4-[2-(2-n-butyl-2-methylphenoxy)ethylamino]-6-chloro-5-methylpyrimidine $n_D^{28}$ 1.5558
130 6-chloro-5-methyl-4-[2-(2-methyl-4-n-pentylphenoxy)ethylamino]pyrimidine mp 42–45
131 6-chloro-5-methyl-4-[2-(2-methyl-4-isopentylphenoxy)ethylamino]pyrimidine mp 96–97
132 6-chloro-4-[2-(4-n-hexyl-2-methylphenoxy)ethylamino]-5-methylpyrimidine mp 76–77
133 6-chloro-4-[2-(4-n-heptyl-2-methylphenoxy)ethylamino]-5-methylpyrimidine mp 72–74
134 6-chloro-5-methyl-4-[2-(2-methyl-4-n-octylphenoxy)ethylamino]pyrimidine mp 72–73
135 6-chloro-4-[2-(2-ethyl-4-methylphenoxy)ethylamino]-5-methylpyrimidine mp 89–92
136 6-chloro-4-chloro-2-methylphenoxy)ethylamino]-5-methylpyrimidine mp 107–109
137 6-chloro-4-[2-(4-chloro-2-ethylphenoxy)ethylamino]-5-methylpyrimidine $n_D^{24}$ 1.5792
138 6-chloro-4-[2-(2-chloro-4-methylphenoxy)ethylamino]-5-methylpyrimidine mp 104–106
139 6-chloro-4-[2-(2-chloro-4-methoxyphenoxy)ethylamino]-5-methylpyrimidine mp 122–124
140 6-chloro-4-[2-(2-chloro-4-trifluoromethylphenoxy)ethylamino]-5-methylpyrimidine mp 102–104
141 6-chloro-4-[2-(2-methoxy-4-methylphenoxy)ethylamino]-5- methylpyrimidine mp 133–135
142 6-bromo-5-methyl-4-(2-phenoxyethylamino)pyrimidine mp 96–98
143 6-bromo-5-methyl-4-[2-(2-methylphenoxy)ethylamino]pyrimidine mp 106–108
144 6-bromo-5-methyl-4-[2-(2-n-propylphenoxy)ethylamino]pyrimidine $n_D^{23}$ 1.5812
145 6-bromo-5-methyl-4-[2-(2-isopropylphenoxy)ethylamino]pyrimidine mp 70–73
146 6-bromo-5-methyl-4-[2-(2-trifluoromethylphenoxy)ethylamino]pyrimidine mp 119–121
147 6-bromo-4-[2-(2,4-dimethylphenoxy)ethylamino]-5-methylpyrimidine mp 81–83
148 6-bromo-5-methyl-4-[2-(2-methyl-5-isopropylphenoxy)ethylamino]pyrimidine $n_D^{23}$ 1.5734
149 6-chloro-5-ethyl-4-(2-phenoxyethylamino)-pyrimidine mp 111–113
150 6-chloro-5-ethyl-4-[2-(2-methylphenoxy)ethylamino]pyrimidine mp 132–134
151 6-chloro-5-ethyl-4-[2-(2-ethylphenoxy)ethylamino]pyrimidine mp 104–106
152 6-chloro-5-ethyl-4-[2-(2-n-propylphenoxy)ethylamino]pyrimidine mp 86–88
153 6-chloro-5-ethyl-4-[2-(2-isopropylphenoxy)ethylamino]pyrimidine mp 95–97
154 4-[2-(2-allylphenoxy)ethylamino]-6-chloro-5-ethylpyrimidine mp 77–79
155 6-chloro-4-[2-(2,4-dimethylphenoxy)ethylamino)]-5-ethylpyrimidine mp 90–92
156 6-chloro-5-ethyl-4-[2-(4-ethyl-2-methylphenoxy)ethylamino]pyrimidine mp 81–82
157 6-chloro-5-ethyl-4-[2-(2-methyl-4-n-propylphenoxy)ethylamino]pyrimidine mp 86–87
158 4-[2-(4-n-butyl-2-methylphenoxy)ethylamino]-6-chloro-5-ethylpyrimidine mp 79–81
159 6-chloro-5-ethyl-4-[2-(2-methyl-4-n-pentylphenoxy)ethylamino]pyrimidine mp 84–85
160 6-chloro-5-ethyl-4-[2-(4-n-heptyl-2-methylphenoxy)ethylamino]pyrimidine mp 83–85
161 6-chloro-4-[2-(4-chloro-2-methylphenoxy)ethylamino)]-5-ethylpyrimidine mp 91–93
162 6-chloro-4-(2-phenoxyethylamino)-5-n-propylpyrimidine mp 110–112
163 6-chloro-5-isopropyl-4-[2-(2-n-propylphenoxy)ethylamino]pyrimidine mp 79–82
164 6-chloro-5-methyl-4-(N-methyl-2-phenoxyethylamino)pyrimidine $n_D^{23}$ 1.5876
165 6-chloro-5-methyl-4-[N-methyl-2-(2-methylphenoxy)ethylamino]pyrimidine $n_D^{23}$ 1.5812
166 5-chloro-6-methyl-4[(N-methyl-2-(2-methyl-4-n-propylphenoxy)ethylamino]pyrimidine $n_D^{23.8}$ 1.5632
167 5-chloro-6-methyl-4-[N-methyl-2-(4-n-butyl-2-methylphenoxy)ethylamino]pyrimidine $n_D^{23.5}$ 1.5579
168 5-chloro-6-methyl-4-[N-methyl-2-(2-methyl-4-n-pentylphenoxy)ethylamino]pyrimidine $n_D^{23.6}$ 1.5482
169 5-chloro-6-methyl-4-[N-methyl-2-(2-methyl-4-n-octylphenoxy)ethylamino]pyrimidine $n_D^{20}$ 1.5228
170 5-bromo-6-methyl-4-[N-methyl-2-(2-methyl-4-n-propylphenoxy)ethylamino]pyrimidine $n_D^{24}$ 1.5730
171 5-bromo-6-methyl-4-[N-methyl-2-(4-n-butyl-2-methylphenoxy)ethylamino]pyrimidine $n_D^{23.6}$ 1.5679
172 5-bromo-6-methyl-4-[N-methyl-2-(2-methyl-4-n-pentylphenoxy)ethylamino]pyrimidine $n_D^{24}$ 1.5622
173 6-chloro-4-(N-ethyl-2-phenoxyethylamino)-5-methylpyrimidine $n_D^{23}$ 1.5729
174 6-chloro-4-[N-ethyl-2-(2-methylphenoxy)ethylamino]-5-methylpyrimidine $n_D^{23}$ 1.5689
175 5-chloro-4-[N-ethyl-2-(2-methyl-4-n-propylphenoxy)ethylamino]-6-methylpyrimidine $n_D^{23.7}$ 1.5542
176 5-chloro-4-[N-ethyl-2-(4-n-butyl-2-methylphenoxy)ethylamino]-6-methylpyrimidine $n_D^{21.5}$ 1.5540
177 5-chloro-4-[N-ethyl-2-(2-methyl-4-n-pentylphenoxy)ethylamino]-6-methylpyrimidine $n_D^{23.2}$ 1.5442
178 5-bromo-4-[N-ethyl-2-(2-methyl-4-n-propylphenoxy)ethylamino]-6-methylpyrimidine $n_D^{21.2}$ 1.5680
179 5-bromo-4-[N-ethyl-2-(4-n-butyl-2-methylphenoxy)ethylamino]-6-methylpyrimidine $n_D^{21.4}$ 1.5635
180 5-bromo-4-[N-ethyl-2-(2-methyl-4-n-pentylphenoxy)ethylamino]-6-methylpyrimidine $n_D^{23.5}$ 1.5550
181 5-chloro-6-methyl-4-[N-n-propyl-2-(2-methyl-4-n-pentylphenoxy)ethylamino]pyrimidine $n_D^{26}$ 1.5444
182 5-chloro-6-methyl-4-(1-methyl-2-phenoxyethylamino)pyrimidine mp 85–87
183 5-chloro-6-methyl-4-[1-methyl-2-(2-methyl-4-n-propylphenoxy)ethylamino]pyrimidine $n_D^{9.5}$ 1.5560
184 5-chloro-6-methyl-4-[1-methyl-2-(4-n-butyl-2-methylphenoxy)ethylamino]pyrimidine
185 5-chloro-6-methyl-4-[1-methyl-2-(2-methyl-4-n-pentylphenoxy)ethylamino]pyrimidine $n_D^{22.5}$ 1.5397
186 5-bromo-6-methyl-4-(1-methyl-2-phenoxy)ethylaminopyrimidine mp 80–82
187 5-bromo-6-methyl-4-[1-methyl-2-(2-methyl-4-n-propylphenoxy)ethylamino]pyrimidine 188 5-bromo-6-methyl-4-[1-methyl-2-(4-n-butyl-2-methylphenoxy)ethylamino]pyrimidine
189 5-bromo-6-methyl-4-[1-methyl-2-(2-methyl-4-n-pentylphenoxy)ethylamino]pyrimidine $n_D^{23.7}$ 1.5503
190 6-chloro-5-methyl-4-(1-methyl-2-phenoxyethylamino)pyrimidine mp 95–97
191 6-chloro-5-methyl-4-[1-methyl-2-(2-methylphenoxy)ethylamino]pyrimidine mp 63–67
192 6-chloro-5-methyl-4-[1-methyl-2-(3-methylphenoxy)ethylamino]pyrimidine mp 110–111
193 6-chloro-5-ethyl-4-(1-methyl-2-phenoxyethylamino)pyrimidine mp 97–99
194 6-bromo-5-methyl-4-(1-methyl-2-phenoxyethylamino)pyrimidine mp 90–92
195 5-chloro-6-methyl-4-[2-methyl-2-(2-methyl-4-n-propylphenoxy)ethylamino]pyrimidine
196 5-chloro-6-methyl-4-[2-methyl-2-(4-n-butyl-2-methylphenoxy)ethylamino]pyrimidine $n_D^{19}$ 1.5520
197 5-chloro-6-methyl-4-[2-methyl-2-(2-methyl-4-n-pentylphenoxy)ethylamino]pyrimidine mp 36–38
198 5-bromo-6-methyl-4-[2-methyl-2-(2-methyl-4-n-propylphenoxy)ethylamino]pyrimidine
199 5-bromo-6-methyl-4-[(2-methyl-2-(4-n-butyl-2-methylphenoxy)ethylamino]pyrimidine $n_D^{19.5}$ 1.5630
200 5-bromo-6-methyl-4-[2-methyl-2-(2-methyl-4-n-pentylphenoxy)ethylamino]pyrimidine $n_D^{17.5}$ 1.5594
201 6-chloro-4-[2,2-dimethyl-2-(2-chlorophenoxy)ethylamino]-5-methylpyrimidine mp 36–39
202 6-chloro-4-[2,2-dimethyl-2-(2-methoxyphenoxy)ethylamino]-5-methylpyrimidine mp 74–76
203 5-chloro-6-methyl-4-[3-(2-methyl-4-n-propylphenoxy)propylamino]pyrimidine mp 73–75
204 4-[3-(4-n-butyl-2-methylphenoxy)propylamino]-5-chloro-6-methylpyrimidine mp 62–65
205 5-chloro-6-methyl-4-[3-(2-methyl-4-n-pentylphenoxy)propylamino]pyrimidine mp 74–76
206 5-bromo-6-methyl-4-[3-(2-methyl-4-n-propylphenoxy)propylamino]pyrimidine mp 67–69
207 5-bromo-4-[3-(4-n-butyl-2-methylphenoxy)propylamino]-6-methylpyrimidine mp 59–61
208 5-bromo-6-methyl-4-[3-(2-methyl-4-n-pentylphenoxy)propylamino]pyrimidine mp 59–61
209 6-chloro-5-methyl-4-(3-phenoxypropylamino)pyrimidine mp 86–87
210 6-chloro-5-methyl-4-[3-(2-methylphenoxy)propylamino]pyrimidine mp 114–116
211 6-chloro-5-methyl-4-[3-(2-isopropylphenoxy)propylamino]pyrimidine mp 111–113
212 4-[3-(3-t-butylphenoxy)propylamino]-6-chloro-5-methylpyrimidine $n_D^{21}$ 1.5570
213 6-chloro-4-[3-(2-methylphenoxy)propylamino]-5-isopropylpyrimidine mp 93–95
214 6-chloro-5-isopropyl-4-[3-(2-isopropylphenoxy)propylamino]pyrimidine mp 74–76
215 6-bromo-5-methyl-4-[3-(2-methylphenoxy)propylamino]pyrimidine mp 97–99
216 5-chloro-6-methyl-4-[4-(2-isopropylphenoxy)butylamino]pyrimidine mp 72–74
217 5-chloro-6-methyl-4-[4-(2-methyl-4-n-propylphenoxy)butylamino]pyrimidine mp 40–42
218 4-[4-(4-n-butyl-2-methylphenoxy)butylamino]-5-chloro-6-methylpyrimidine mp 82–84
219 5-chloro-6-methyl-4-[4-(2-methyl-4-n-pentylphenoxy)butylamino]pyrimidine mp 75–77
220 5-bromo-6-methyl-4-[4-(2-methyl-4-n-propylphenoxy)butylamino]pyrimidine mp 41–42
221 5-bromo-4-[4-(4-n-butyl-2-methylphenoxy)butylamino]-6-methylpyrimidine mp 76–78
222 5-bromo-6-methyl-4-[4-(2-methyl-4-n-pentylphenoxy)butylamino]pyrimidine mp 79–81
223 6-chloro-5-methyl-4-[4-(2-isopropylphenoxy)butylamino]pyrimidine mp 99–101
224 6-chloro-5-methyl-4-[5-(2-isopropylphenoxy)pentylamino]pyrimidine mp 97–99
225 6-chloro-4-[2-(4-chlorobenzyloxy)ethylamino]-5-methylpyrimidine mp 114–116
226 6-chloro-5-methyl-4-[2-(4-methylbenzyloxy)ethylamino]pyrimidine mp 102–104
227 6-chloro-4-[2-(3,4-dichlorobenzyloxy)ethylamino]-5-methylpyrimidine mp 100–101
228 6-chloro-5-methyl-4-[N-methyl-2-(4-chlorobenzyloxy)ethylamino]pyrimidine mp 52–54
229 5-chloro-6-methyl-4-[2-(2-methyl-4-n-pentylphenoxy)ethylamino]pyrimidine hydrochloride mp 149–152
230 5-chloro-6-methyl-4-[2-(2-methyl-4-n-pentylphenoxy)ethylamino]pyrimidine nitrate
231 5-chloro-4-[2-(2,4,5-trichlorophenoxy)ethylamino]-6-methylpyrimidine mp 138–142
232 5-chloro-4-[2-(2,4,6-trichlorophenoxy)ethylamino]-6-methylpyrimidine mp 117–119
233 4-[2-(2,4,6-tribromophenoxy)ethylamino]-5-chloro-6-methylpyrimidine mp 160–163
234 5-chloro-6-methyl-4-[2-(2,3,5-trimethylphenoxy)ethylamino]pyrimidine mp 126–128
235 5-chloro-6-methyl-4-[2-(2,3,6-trimethylphenoxy)ethylamino]pyrimidine mp 82–85
236 5-chloro-6-methyl-4-[2-(2,4,6-trimethylphenoxy)ethylamino]pyrimidine mp 62–65
237 5-chloro-4-[2-(4-chloro-3,5-dimethylphenoxy)ethylamino]-6-methylpyrimidine mp 145–146
238 5-chloro-4-[2-(2-chloro-6methyl-4-n-propylphenoxy)ethylamino]-6-methylpyrimidine mp 53–55
239 4-[2-(4-n-butyl-2-chloro-6-methylphenoxy)ethylamino]-5-chloro-6-methylpyrimidine $n_D^{13}$ 1.5650
240 5-chloro-4-[2-(2-chloro-6-methyl-4-n-pentylphenoxy)ethylamino]-6-methylpyrimidine $n_D^{13}$ 1.5609
241 4-[2-(4-isobutyl-2-chloro-6-methylphenoxy)ethylamino]-5-chloro-6-methylpyrimidine mp 60–62
242 5-chloro-6-methyl-4-[2-(2,6-dimethyl-4-n-propylphenoxy)ethylamino]pyrimidine mp 46–48
243 4-[2-(4-n-butyl-2,6-dimethylphenoxy)ethylamino]-5-chloro-6-methylpyrimidine mp 37–39
244 5-chloro-6-methyl-4-[2-(2,6-dimethyl-4-n-pentylphenoxy)ethylamino]pyrimidine $n_D^{20}$ 1.5470
245 5-bromo-4-[2-(2,4,6-trichlorophenoxy)ethylamino]-6-methylpyrimidine mp 120–123
246 5-bromo-4-[2-(2-chloro-6-methyl-4-n-pentylphenoxy)ethylamino]-6-methylpyrimidine $n_D^{13}$ 1.5717
247 5-bromo-6-methyl-4-[2-(2,6-dimethyl-4-n-pentylphenoxy)ethylamino]pyrimidine mp 44–46
248 4-{N-n-butyl-N-[2-(2-methyl-4-n-pentylphenoxy)ethyl]amino}-5-chloro-6-methylpyrimidine $n_D^{24.5}$ 1.5402
249. 5-chloro-6-methyl-4-[2-(2-methyl-4-n-propylphenoxy)ethylamino]pyrimidine nitrate mp 117–120 (decomposition)

250. 5-chloro-6-methyl-4-[2-(2-methyl-4-sec-butylphenoxy)ethylamino]pyrimidine $n_D^{20}$ 1.5604
251. 5-chloro-6-methyl-4-[2-(2-methyl-4-n-butylphenoxy)ethylamino]pyrimidine nitrate mp 115–118 (decomposition)
252. 5-chloro-6-methyl-4-[2-(2-methyl-4-sec-pentylphenoxy)ethylamino]pyrimidine $n_D^{20}$ 1.5548
253. 5-chloro-6-methyl-4-[2-(2-methyl-4-allylphenoxy)ethylamino]pyrimidine mp 35–38
254. 5-chloro-6-methyl-4-[2-(2,4-dimethyl-6-nitrophenoxy)ethylamino]pyrimidine mp 77–80
255. 5-chloro-6-methyl-4-[2-(2-methyl-4-n-butyl-6-nitrophenoxy)ethylamino]pyrimidine $n_D^{22}$ 1.5621
256. 5-chloro-6-methyl-4-[2-(2-methyl-4-n-pentyl-6-nitrophenoxy)ethylamino]pyrimidine mp 146–148
257. 5-chloro-6-methyl-4-[2-(2-methyl-4-chloro-6-nitrophenoxy)ethylamino]pyrimidine nitrate mp 107–109 (decomposition)
258. 5-chloro-6-methyl-4-[2-(2-ethyl-4-methylphenoxy)ethylamino]pyrimidine mp 59–61
259. 5-chloro-6-methyl-4-[2-(2,4-diethylphenoxy)ethylamino]pyrimidine $n_D^{29}$ 1.5612
260. 5-chloro-6-methyl-4-[2-(2-ethyl-4-n-propylphenoxy)ethylamino]pyrimidine $n_D^{27}$ 1.5562
261. 5-chloro-6-methyl-4-[2-(2-ethyl-4-isopropylphenoxy)ethylamino]pyrimidine $n_D^{29}$ 1.5554
262. 5-chloro-6-methyl-4-[2-(2-ethyl-4-n-butylphenoxy)ethylamino]pyrimidine $n_D^{27}$ 1.5478
263. 5-chloro-6-methyl-4-[2-(2-ethyl-4-n-pentylphenoxy)ethylamino]pyrimidine nitrate mp 129–131 (decomposition)
264. 5-chloro-6-methyl-4-[2-(2-ethyl-4-sec-butylphenoxy)ethylamino]pyrimidine $n_D^{26.4}$ 1.5545
265. 5-chloro-6-methyl-4-[2-(2-ethyl-4-n-pentylphenoxy)ethylamino]pyrimidine $n_D^{27.1}$ 1.5462
266. 5-chloro-6-methyl-4-[2-(2,6-diethyl-4-n-butylphenoxy)ethylamino]pyrimidine
267. 5-chloro-6-methyl-4-[2-(2-ethyl-4,6-di-n-pentylphenoxy)ethylamino]pyrimidine
268. 5-chloro-6-methyl-4-[2-(2,4,6-triisopropylphenoxy)ethylamino]pyrimidine
269. 5-chloro-6-methyl-4-[2-(2,3,4,5-tetrachlorophenoxy)ethylamino]pyrimidine
270. 5-chloro-6-methyl-4-[2-(2,3,4,5,6-pentachlorophenoxy)ethylamino]pyrimidine
271. 5-chloro-6-methyl-4-[2-(2,3,6-trimethyl-4-n-propylphenoxy)ethylamino]pyrimidine
272. 5-chloro-6-methyl-4-[2-(2,3,6-trimethyl-4-n-butylphenoxy)ethylamino]pyrimidine
273. 5-chloro-6-methyl-4-[2-(2,3,6-trimethyl-4-n-pentylphenoxy)ethylamino]pyrimidine
274. 5-chloro-6-methyl-4-[2-(2,3,6-trimethyl-4-chlorophenoxy)ethylamino]pyrimidine
275. 5-chloro-6-methyl-4-[2-(2,3,5,6-tetramethyl-4-n-propylphenoxy)ethylamino]pyrimidine
276. 5-bromo-6-methyl-4-[2-(2-ethyl-4-chlorophenoxy)ethylamino]pyrimidine $n_D^{29}$ 1.5939
277. 5-bromo-6-methyl-4-[2-(2-ethyl-4-methylphenoxy)ethylamino]pyrimidine $n_D^{28.8}$ 1.5812
278. 5-bromo-6-methyl-4-[2-(2,4-diethylphenoxy)ethylamino]pyrimidine $n_D^{28.6}$ 1.5742
279. 5-bromo-6-methyl-4-[2-(2-ethyl-4-n-propylphenoxy)ethylamino]pyrimidine $n_D^{27}$ 1.5662
280. 5-bromo-6-methyl-4-[2-(2-ethyl-4-isopropylphenoxy)ethylamino]pyrimidine $n_D^{29}$ 1.5671
281. 5-bromo-6-methyl-4-[2-(2-ethyl-4-n-butylphenoxy)ethylamino]pyrimidine $n_D^{27.2}$ 1.5578
282. 5-bromo-6-methyl-4-[2-(2-ethyl-4-sec-butylphenoxy)ethylamino]pyrimidine $n_D^{28}$ 1.5678
283. 5-bromo-6-methyl-4-[2-(2-ethyl-4-n-pentylphenoxy)ethylamino]pyrimidine $n_D^{26.2}$ 1.5583
284. 5-bromo-6-methyl-4-[N-n-propyl-2-(2-methyl-4-pentylphenoxy)ethylamino]pyrimidine $n_D^{26}$ 1.5550
285. 6-chloro-5-methyl-4-[2-(2,6-dimethyl-4-n-butylphenoxy)ethylamino]pyrimidine mp 89–91
286. 6-chloro-5-methyl-4-[2-(2-ethyl-4-n-butylphenoxy)ethylamino]pyrimidine mp 55–57
287. 6-chloro-5-methyl-4-[2-(2-ethyl-4-n-pentylphenoxy)ethylamino]pyrimidine mp 60–62
288. 6-chloro-5-methyl-4-[2-(2-methyl-4-allylphenoxy)ethylamino]pyrimidine mp 63–66
289. 4-[2-(2-methyl-4-n-propylphenoxy)ethylamino]-5,6-trimethylenepyrimidine mp 90–91
290. 4-[2-(2-methyl-4-n-butylphenoxy)ethylamino]-5,6-trimethylenepyrimidine mp 82–84
291. 4-[2-(2-methyl-4-n-pentylphenoxy)ethylamino]-5,6-trimethylenepyrimidine mp 87–89
292. 4-[2-(2-ethyl-4-n-propylphenoxy)ethylamino]-5,6-trimethylenepyrimidine mp 107–109
293. 4-[2-(2-ethyl-4-n-butylphenoxy)ethylamino]-5,6-trimethylenepyrimidine mp 87–89
294. 4-[2-(2-ethyl-4-n-pentylphenoxy)ethylamino]-5,6-trimethylenepyrimidine mp 80–82
295. 4-[2-(2-methyl-4-n-propyl-6-chlorophenoxy)ethylamino]-5,6-trimethylenepyrimidine mp 125–127
296. 4-[2-(2-methyl-4-allylphenoxy)ethylamino]-5,6-trimethylenepyrimidine mp 108–110
297. 4-[1-methyl-2-(2-methyl-4-n-propylphenoxy)ethylamino]-5,6-trimethylenepyrimidine mp 120–122
298. 4-[2-(2-methyl-4-n-butylphenoxy)ethylamino]-5,6-tetramethylenepyrimidine
299. 5-chloro-6-methyl-4-benzylaminopyrimidine mp 124–126
300. dl-5-chloro-6-methyl-4-α-methylbenzylaminopyrimidine mp 94–96
301. dl-5-chloro-6-methyl-4-(α-methyl-2-metoxybenzylamino)pyrimidine mp 81–84
302. dl-5-chloro-6-methyl-4-(α-methyl-4-methylbenzylamino)pyrimidine mp 50–53
303. dl-5-chloro-6-methyl-4-(α-methyl-4-chlorobenzylamino)pyrimidine mp 74–76
304. dl-5-chloro-6-methyl-4-(α-methyl-4-bromobenzylamino)pyrimidine mp 87–89
305. dl-5-chloro-6-methyl-4-(α-methyl-4-methoxybenzylamino)pyrimidine mp 90–93
306. dl-5-chloro-6-methyl-4-(α-methyl-2,5-dimethoxybenzylamino)pyrimidine mp 88–90
307. dl-5-chloro-6-methyl-4-(α-ethylbenzylamino)pyrimidine $n_D^{20}$ 1.5725
308. 5-chloro-6-methyl-4-phenethylaminopyrimidine mp 81–83
309. dl-5-chloro-6-n-propyl-4-(α-ethylbenzylamino)pyrimidine $n_D^{19}$ 1.5650
310. dl-5-chloro-6-methyl-4-(α-methyl-2-methylbenzylamino)pyrimidine mp 121–124
311. dl-5-chloro-6-methyl-4-(α-methyl-4-ethylbenzylamino)pyrimidine mp 72–73
312. dl-5-chloro-6-methyl-4-(α-methyl-2,4-dimethylbenzylamino)pyrimidine mp 124–126
313. 5-bromo-6-methyl-4-benzylaminopyrimidine mp 108–111
314. dl-5-bromo-6-methyl-4-(α-methylbenzylamino)pyrimidine mp 85–87

315. dl-5-bromo-6-methyl-4-(α-methyl-2-methoxybenzylamino)pyrimidine mp 71-75
316. dl-5-bromo-6-methyl-4-(α-ethylbenzylamino)pyrimidine $n_D^{20}$1.5898
317. dl-5-bromo-6-methyl-4-phenethylaminopyrimidine mp 63-65
318. dl-5-bromo-6-methyl-4-(3-phenylbutylamino)pyrimidine mp 62-64
319. dl-5-bromo-6-n-propyl-4-(α-ethylbenzylamino)primidine $n_D^{22}$1.5769
320. dl-5-bromo-6-methyl-4-(α-ethyl-4-methylbenzylamino)pyrimidine $n_D^{22}$1.5840
321. dl-5-bromo-6-methyl-4-(α-ethyl-2,4-dichlorobenzylamino)pyrimidine $n_D^{22}$1.6020
322. 6-chloro-5-methyl-4-benzylaminopyrimidine mp 174-176
323. 6-chloro-5-methyl-4-(2-methoxybenzylamino)pyrimidine mp 126-128
324. D-(−)-6-chloro-5-methyl-4-(α-methylbenzylamino)pyrimidine mp 97-99 $[\alpha]_D$−4.9 (c=2,CH$_3$OH)
325. L-(+)-6-chloro-5-methyl-4-(α-methylbenzylamino)pyrimidine mp 97-99 $[\alpha]_D$+5.1 (c=2, CH$_3$OH)
326. dl-6-chloro-5-methyl-4-(α-methylbenzylamino)pyrimidine mp 96-97
327. dl-6-chloro-5-methyl-4-(α-methyl-2-methylbenzylamino)pyrimidine mp 150-152
328. dl-6-chloro-5-methyl-4-(α-methyl-2-chlorobenzylamino)pyrimidine mp 147-149
329. dl-6-chloro-5-methyl-4-(α-methyl-2-methoxybenzylamino)pyrimidine mp 125-126
330. dl-6-chloro-5-methyl-4-(α-methyl-2-ethoxybenzylamino)pyrimidine mp 89-92
331. dl-6-chloro-5-methyl-4-(α-methyl-2-n-propoxybenzylamino)pyrimidine mp 58-60
332. dl-6-chloro-5-methyl-4-(α-methyl-3-methoxybenzylamino)pyrimidine mp 71-73
333. dl-6-chloro-5-methyl-4-(α-methyl-4-methylbenzylamino)pyrimidine mp 97-100
334. dl-6-chloro-5-methyl-4-(α-methyl-4-chlorobenzylamino)pyrimidine mp 126-128
335. dl-6-chloro-5-methyl-4-(α-methyl-4-methoxybenzylamino)pyrimidine mp 100-102
336. dl-6-chloro-5-methyl-4-(α-ethylbenzylamino)pyrimidine mp 67-69
337. dl-6-chloro-5-methyl-4-(α-ethyl-4-chlorobenzylamino)pyrimidine mp 92-93
338. dl-6-chloro-5-methyl-4-(α-isopropylbenzylamino)pyrimidine mp 71-73
339. 6-chloro-5-methyl-4-phenethylaminopyrimidine mp 130-132
340. dl-6-chloro-5-methyl-4-(β-isopropyl-4-chlorophenethylamino)pyrimidine mp 126-128
341. dl-6-chloro-5-methyl-4-(3-phenylbutylamino)pyrimidine mp 103-105
342. dl-6-chloro-5-methyl-4-(α-methyl-4-n-pentylbenzylamino)pyrimidine
343. dl-6-chloro-5-methyl-4-(α-methyl-2,4-dichlorobenzylamino)pyrimidine mp 108-111
344. dl-6-chloro-5-methyl-4-(α-methyl-4-ethylbenzylamino)pyrimidine mp 105-107
345. dl-6-chloro-5-methyl-4-(α-methyl-2,4-dimethylbenzylamino)pyrimidine mp 128-130
346. 6-chloro-5-ethyl-4-benzylaminopyrimidine mp 153-155
347. 6-chloro-5-ethyl-4-(3-chlorobenzylamino)pyrimidine mp 135-137
348. dl-6-chloro-5-ethyl-4-(α-methylbenzylamino)pyrimidine mp 111-113
349. dl-6-chloro-5-ethyl-4-(α-methyl-2-methoxybenzylamino)pyrimidine mp 105-110
350. dl-6-chloro-5-ethyl-4-(α-methyl-2-n-propoxybenzylamino)pyrimidine mp 80-81
351. dl-6-chloro-5-ethyl-4-(α-methyl-4-methylbenzylamino)pyrimidine mp 89-92
352. dl-6-chloro-5-ethyl-4-(α-methyl-4-methoxybenzylamino)pyrimidine mp 85-88
353. dl-6-chloro-5-ethyl-4-(α-ethylbenzylamino)pyrimidine mp 65-68
354. 6-chloro-5-ethyl-4-phenethylaminopyrimidine mp 118-120
355. dl-6-chloro-5-ethyl-4-(α-methyl-2,4-dimethylbenzylamino)pyrimidine mp 115-117
356. dl-6-chloro-5-ethyl-4-(α-methyl-3,4-dichlorobenzylamino)pyrimidine mp 105-107
357. dl-6-chloro-5-ethyl-4-(α-methyl-4-chlorobenzylamino)pyrimidine mp 95-97
358. dl-6-chloro-5-n-propyl-4-(α-methylbenzylamino)pyrimidine mp 91-92
359. dl-6-chloro-5-isopropyl-4-(α-methylbenzylamino)pyrimidine mp 100-102
360. dl-6-chloro-5-isopropyl-4-(α-methyl-2-methoxybenzylamino)pyrimidine mp 85-87
361. dl-6-chloro-5-n-propyl-4-(α-methyl-4-chlorobenzylamino)pyrimidine mp 103-106
362. dl-6-chloro-5-n-propyl-4-(α-methyl-2-methylbenzylamino)pyrimidine mp 108-111
363. dl-6-chloro-5-n-propyl-4-(α-methyl-4-methylbenzylamino)pyrimidine mp 79-82
364. dl-6-bromo-5-methyl-4-(α-methylbenzylamino)pyrimidine mp 101-103
365. dl-6-bromo-5-methyl-4-(α-methyl-2-methoxybenzylamino)pyrimidine mp 122-125
366. dl-6-bromo-5-methyl-4-(α-methyl-2-ethoxybenzylamino)pyrimidine mp 101-103
367. dl-6-bromo-5-methyl-4-(α-methyl-4-methylbenzylamino)pyrmidine mp 106-108
368. dl-6-bromo-5-methyl-4-(α-methyl-4-chlorobenzylamino)pyrimidine mp 135-138
369. dl-6-bromo-5-methyl-4-(α-methyl-4-methoxybenzylamino)pyrimidine mp 99-102
370. dl-6-bromo-5-methyl-4-(α-ethylbenzylamino)pyrimidine mp 98-99
371. dl-6-bromo-5-methyl-4-(α-methyl-2,4-dichlorobenzylamino)pyrimidine mp 124-126
372. dl-5,6-dimethyl-4-α-methylbenzylaminopyrimidine mp 115-117
373. 5-bromo-6-methyl-4-furfurylaminopyrimidine mp 69-70
374. 6-chloro-5-methyl-4-furfurylaminopyrimidine mp 126-128
375. 6-chloro-5-ethyl-4-furfurylaminopyrimidine mp 111-113
376. 6-chloro-5-isopropyl-4-furfurylaminopyrimidine mp 108-110
377. dl-6-chloro-5-methyl-4-(α-methyl-2-thenylamino)pyrimidine mp 93-96
378. dl-6-bromo-5-methyl-4-(α-methyl-2-thenylamino)pyrimidine mp 106-107
379. dl-6-chloro-5-ethyl-4-(α-methyl-2-thenylamino)pyrimidine mp 112-115
380. dl-6-chloro-5-isopropyl-4-(α-methyl-2-thenylamino)pyrimidine mp 97-99
381. dl-5-chloro-6-methyl-4-(α-ethyl-4-methylbenzylamino)pyrimidine $n_D^{22.5}$1.5728

382. dl-5-chloro-6-methyl-4-(α-ethyl-2-methoxybenzylamino)pyrimidine $n_D^{29}$ 1.5713
383. dl-5-chloro-6-methyl-4-(α-ethyl-4-chlorobenzylamino)pyrimidine $n_D^{29.4}$ 1.5825
384. dl-5-chloro-6-methyl-4-(α-ethyl-2,4-dichlorobenzylamino)pyrimidine $n_D^{22.5}$ 1.5857
385. dl-bromo-6-methyl-4-(α-methyl-4-methoxybenzylamino)pyrimidine $n^{22}$ 1.5982
386. L-(+)-6-chloro-5-ethyl-4-(α-methylbenzylamino)pyrimidine mp 111–113
387. dl-6-chloro-5-methyl-4-(N,-α-dimethylbenzylamino)pyrimidine $n^{19}$ 1.5856
388. dl-6-chloro-5-methyl-4-(α-ethyl-4-ethylbenzylamino)pyrimidine $n_D^{28.1}$ 1.5776
389. dl-4-[α-methylbenzylamino]-5,6-trimethylenepyrimidine mp 132–134
390. dl-4-(α-ethyl-4-methoxybenzylamino)-5,6-trimethylenepyrimidine mp 109–111

Compounds of the formula (I) in accordance with the present invention may readily be prepared by a process provided by the invention and illustrated below. The process comprises the steps of reacting a compound of formula (IV)

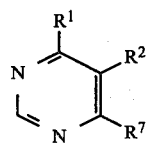

(IV)

[wherein $R^1$ and $R^2$ are as defined and $R^7$ is a leaving group], with a compound of formula (V)

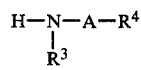

(V)

[wherein $R^3$, A and $R^4$ are as defined], and optionally salifying the resultant compound.

The reaction is an analogy procedure and the nature of the leaving group $R^7$ is not critical. $R^7$ can be, for example, a halogen atom or an alkylthio group, or it can be any other leaving group employed for an analogous reaction. The present reaction may be performed under per se known conditions, suitably in the presence of a base and in the presence or absence of a solvent.

Where a solvent is used, there is no special limitation provided it does not interfere with the reaction. Suitable solvents include, for example, chlorinated or non-chlorinated aromatic, aliphatic or alicyclic hydrocarbons (for example, benzene, toluene, xylene, methylnaphthalene, petroleum ether, ligroin, hexane, chlorobenzene, dichlorobenzene, methylene chloride, chloroform, dichloroethane, trichloroethylene or cyclohexane), ethers (for example, diethyl ether, ethylene glycol dimethyl ether, tetrahydrofuran or dioxane), ketones (for example, acetone or methyl ethyl ketone), alcohols (for example, methanol, ethanol or ethylene glycol), amides such as N,N-dimethylformamide or N.N-dimethylacetamide; higher alcohols; other polar solvents such as dimethylsulphoxide and pyridine; or mixtures of such solvents with each other or with water.

Examples of suitable bases employed in preferred embodiments of the present process include organic bases such as triethylamine, pyridine or N,N-diethylaniline, and inorganic bases such as sodium hyroxide, potassium hydroxide, sodium carbonate or potassium carbonate.

The reaction temperature is not critical, but will usually be from above ambient temperature up to the reflux temperature of the solvent used; it is preferable to perform the reaction with heating in order to shorten the reaction period. Alternatively, when no solvent is used, the reaction may be performed by melting reactants with heating, typically for instance to about 200° C. More generally the reaction is usually carried out at from 100° to 200° C.

Upon completion of the reaction, the desired product may optionally be purified by conventional means, such as by the use of recrystallization and/or chromatographic techniques.

In accordance with one aspect of the process of this invention, a compound of formula (II):

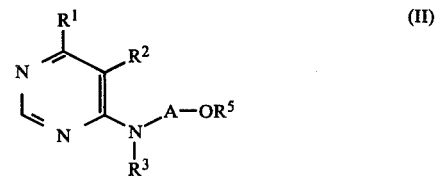

(II)

wherein $R^1$, $R^2$, $R^3$, $R^5$ and A are as defined above) is prepared. The process then comprises reacting a compound of formula (VI)

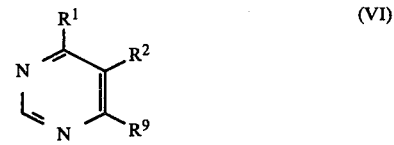

(VI)

[wherein $R^1$ and $R^2$ are as defined and $R^9$ is selected from halogen atoms and methylthio groups], with a compound of formula (VII)

(VII)

[wherein $R^3$, A and $R^5$ are as defined], and optionally salifying the resultant compound.

In accordance with another aspect of the process of this invention, a compound of formula (III):

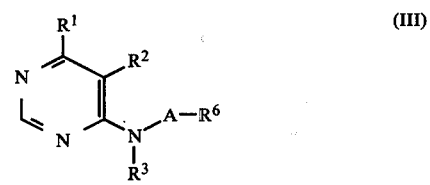

(III)

wherein $R^1$, $R^2$, $R^3$, $R^6$ and A are as defined above) is prepared. The process then comprises reacting a compound of formula (VIII)

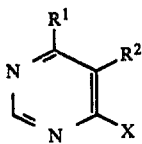

[wherein $R^1$ and $R^2$ are as defined and X is a halogen atom], with a compound of formula (VII)

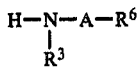

[wherein $R^3$, A and $R^6$ are as defined], and optionally salifying the resultant compound.

In general, the reaction conditions will preferably as previously described; however for the preparation of compounds of formula (II) using a compound (VI) where $R^9$ is a methylthio group the reaction is preferably performed in an inert organic solvent with heating. The solvent is then preferably selected from: aromatic hydrocarbons such as toluene and xylene; chlorinated aromatic hydrocarbons such as chlorobenzene, dichlorobenzene and chlorotoluene; ethers such as dioxane; amides such as N,N-dimethylformamide and N,N-dimethylacetamide; higher alcohols; dimethylsulphoxide and pyridine. More preferably the solvent is one having a boiling point of from 100°–200° C., for example N,N-dimethylformamide, N,N-dimethylacetamide or dimethylsulphoxide.

Acid addition salts of compounds of formula (I) may readily be prepared by introducing an acid into the reaction mixture, then by distilling off any solvent.

The preparation of compounds according to the invention is illustrated by the following Preparative Examples.

PREPARATIVE EXAMPLE 1

6-chloro-5-methyl-4-[2-(2-methyl-4-n-pentylphenoxy)ethylamino]pyrimidine (compound number 130)

To a solution of 3.2 g (0.02 mol) of 4,6-dichloro-5-methylpyrimidine in 50 ml of toluene were added 2.0 g (0.02 mol) of triethylamine and 4.4 g (0.02 mol) of 2-(2-methyl-4-n-pentylphenoxy)ethylamine. The mixture was then refluxed with stirring for 5 hours.

Upon completion of the reaction, the product was washed with water, dried over anhydrous sodium sulphate, and the toluene was distilled off under reduced pressure, leaving an oil. The oil was isolated by column chromatography (Wakogel C-200, using elution with a 1:1 by volume mixture of benzene and ethyl acetate) to give crystals which were recrystallized from n-hexane to give 5.1 g of the desired product in the form of colourless needles melting at 42°–45° C.

PREPARATIVE EXAMPLE 2

5-chloro-6-methyl-4-[2-(2-methyl-4-n-pentylphenoxy)ethylamino]-pyrimidine (compound number 54)

To a solution of 3.2 g (0.02 mol) of 4,5-dichloro-6-methylpyrimidine in 50 ml of benzene were added 2.0 g (0.02 mol) of triethylamine and 4.4 g (0.02 mol) of 2-(2-methyl-4-n-pentylphenoxy)ethylamine. The mixture was then refluxed with stirring for 4 hours.

Upon completion of the reaction, the reaction mixture was treated in the same manner as in Preparative Example 1, affording 5.3 g of the desired product in the form of a pale yellow oil, $n_D^{25} 1.5530$

PREPARATIVE EXAMPLE 3

5,6-dimethyl-4-[2-(2-methyl-4-n-propylphenoxy)ethylamino]pyrimidine (compound number 13)

To a solution of 2.8 g (0.02 mol) of 4-chloro-5,6-dimethylpyrimidine in 50 ml of xylene were added 2.0 g (0.02 mol) of triethylamine and 3.9 g (0.02 mol) of 2-(2-methyl-4-n-propylphenoxy)ethylamine, and the mixture was refluxed, with stirring, for 12 hours.

Upon completion of the reaction, the reaction mixture was treated in the same manner as in Preparative Example 1, giving 3.9 g of the desired product in the form of colourless prisms melting at 71°–73° C.

PREPARATIVE EXAMPLE 4

5-chloro-6-methyl-4-[N-methyl-2-(2-methyl-4-n-propylphenoxy)ethylamino]pyrimidine (compound number 166)

To a solution of 3.2 g (0.02 mol) of 4,5-dichloro-6-methylpyrimidine were added 2.0 g (0.02 mol) of triethylamine and 4.7 g (0.02 mol) of N-methyl-2-(2-methyl-4-n-propylphenoxy)ethylamine, and the mixture was melt-reacted by heating it for 5 minutes on a heater.

Upon completion of the reaction, 100 ml of benzene were added to the reaction mixture, and insoluble matters were filtered off. The filtrate was washed with water, dried over anhydrous sodium sulphate, and the benzene distilled off under reduced pressure, leaving an oil. The oil was isolated by column chromatography (Wakogel C-200, eluted with a 3:1 by volume mixture of benzene and ethyl acetate) to give 6.1 g of the desired product in the form of a pale yellow oil $n_D^{23.8} 1.5632$

PREPARITIVE EXAMPLE 5

4-[2-(2-methyl-4-n-pentylphenoxy)ethylamino]-5,6-trimethylenepyrimidine (compound number 291)

3.1 g (0.02 mol) of 4-chloro-5,6-trimethylenepyrimidine, 4.4 g (0.02 mol) of 2-(2-methyl-4-n-pentylphenoxy)ethylamine and 2 g (0.02 mol) of triethylamine were dissolved in 50 ml of ethanol, and the solution was refluxed for 2 days. At the end of this period, water was added to the reaction mixture which was then extracted with benzene. The benzene layer was washed with water and dried over anhydrous sodium sulphate. The benzene was removed by distillation and the residue was recrystallized from a mixture of hexane and benzene to give 3.6 g of the desired compound in the form of colourless needles melting at 87°–89° C.

Elementary analysis: Calculated for $C_{21}H_{29}N_3O$: C, 74.30%; H, 8.61% N, 12.38%. Found: C, 74.50%; H, 8.60%; N, 12.25%.

PREPARATIVE EXAMPLE 6 dl-5-bromo-6-methyl-4-(α-methylbenzylamino)pyrimidine (compound number 314)

2.0 g (0.02 mol) of triethylamine and 2.4 g (0.02 mol) of dl-α-methylbenzylamine were added to a solution of 4.15 g (0.02 mol) of 5-bromo-4-chloro-6-methyl-pyrimidine in 50 ml of benzene, and the mixture was refluxed with stirring for 5 hours. Upon completion of the reaction, the reaction product was washed with water, dried over anhydrous sodium sulphate and the benzene was distilled off to leave an oil. This oil was then caused to crystallize using column chromatography (Wakogel C-200, eluted with a 1:1 mixture of benzene and ethyl acetate).

Crystals were obtained and recrystallized from n-hexane to give 2.6 g of the desired product in the form of pale yellow prisms melting at 85°–87° C.

PREPARATIVE EXAMPLE 7

L-(+)-6-chloro-5-methyl-4-(α-methylbenzylamino)-pyrimidine (compound number 325)

A mixture of 6.52 g (0.04 mol) of 4,6-dichloro-5-methylpyrimidine, 4.8 g (0.04 mol) of L-(−)-α-methylbenzylamine and 4.0 g (0.04 mol) of triethylamine was heated and melted on a heater in the absence of a solvent. Upon completion of the reaction, 100 ml of benzene were added to the reaction mixture and the resulting solution was washed with water. The benzene was distilled off to leave crystals, which were recrystallized from a 1:1 mixture of benzene and n-hexane to give 4.8 g of the desired product in the form of a colourless powder melting at 97°–99° C.

PREPARATIVE EXAMPLE 8 dl-6-chloro-5-methyl-4-(α-methylbenzylamino)pyrimidine (compound number 326)

To a solution of 6.52 g (0.04 mol) of 4,6-dichloro-5-methylpyrimidine in 100 ml of benzene were added 4.0 g (0.04 mol) of triethylamine and 4.8 g (0.04 mol) of dl-α-methylbenzylamine, and the mixture was refluxed for 40 hours. Upon completion of the reaction, the reaction mixture was washed with water and dried over anhydrous sodium sulphate. The benzene was distilled off under reduced pressure to give crystals which were then recrystallized from a mixture of benzene and n-hexane, affording 3.5 g of the desired product in the form of colourless sandy crystals melting at 96°–97° C.

PREPARATIVE EXAMPLE 9 dl-6-chloro-5-methyl-4-(α-methyl-2-methoxybenzylamino)pyrimidine (compound number 329)

To a solution of 3.26 g (0.02 mol) of 4,6-dichloro-5-methylpyrimidine in 50 ml of toluene were added 2.0 g (0.02 mol) of triethylamine and 3.0 g (0.02 mol) of dl-α-methyl-2-methoxybenzylamine, and the mixture was refluxed with stirring for 20 hours. Upon completion of the reaction, the reaction mixture was washed in turn with diluted aqueous hydrochloric acid, a diluted aqueous solution of sodium hydroxide, and water, and then dried over anhydrous sodium sulphate. The toluene was distilled off under reduced pressure to leave crystals, which were recrystallized from a mixture of benzene and n-hexane, giving 2.7 g of the desired product in the form of colourless sandy crystals melting at 125°–126° C.

PREPARATIVE EXAMPLE 10 dl-6-bromo-5-methyl-4-(α-methylbenzylamino)pyrimidine (compound 364)

In a solution of 5.0 g (0.02 mol) of 4,6-dibromo-5-methylpyrimidine in 50 ml of toluene were dissolved 2.0 g (0.02 mol) of triethylamine and 2.4 g (0.02 mol) of dl-α-methylbenzylamine, and the mixture was refluxed with stirring for 10 hours. Upon completion of the reaction, the reaction mixture was treated in the same manner as in Preparative Example 8 to give crystals, which were recrystallized from benzene to give 3.8 g of the desired product in the form of pale yellow prisms melting at 101°–103° C.

Compounds of the invention have a potent activity against harmful bacteria and fungi which are parasitic to agricultural and horticultural plants. They are highly effective, for example, against blast, Helminthosporium leaf spot and sheath blight in rice plant, late blight and early blight in tomatoes, anthracnose, downy mildew and powdery mildew in cucumbers and various soil-borne diseases caused by Fusarium. Compounds of the invention also have a strong acaricidal activity, for example, against adults and eggs of Tetranychus, Panonychus and rust mites which are parasitic to fruit trees, vegetables and flowers; Ixodidac, Dermanysside and Sarcoptidae parasitic to animals. Further, they are active against exoparasites such as Oestrus, Lucilia, Hypoderma, Gautrophilus, lice and fleas which are parasitic to animals and birds; domestic insects such as cockroaches and house flies; and various harmful insects in agricultural and horticultural areas such as aphids, diamondback moths and juvenile Lepidoptera. They are also active against various pathogenic fungi parasitic to human beings and animals, and are also effective against various soil borne bacteria and fungi.

Reflecting the activity of the present compounds, the invention further provides compositions which contain one or more compounds of formula (I), together with a carrier and optionally other auxiliary agents, if necessary. The present compositions may be formulated as preparations of the type commonly employed for agricultural, horticultural, veterinary or medicinal use, for instance as dusts, coarse dusts, microgranules, fine microgranules, wettable powders, emulsifiable concentrates, aqueous or oily suspensions, and aerosols.

The carrier employed may be natural or synthetic and organic or inorganic; it is generally employed to assist the active ingredient to reach the substrate to be treated, and to make it easier to store, transport or handle the active compound.

Suitable solid carriers include:

inorganic substances, such as clays (examples of which are kaolinite, montmorillonite and attapulgite), talc, mica, pyrophyllite, pumice, vermiculite, gypsum, calcium carbonate, dolomite, diatomaceous earth, magnesium carbonate, apatite, zeolite, silicic anhydride and synthetic calcium silicate; vegetable organic substances, such as soybean meal, tobacco powder, walnut powder, wheat flour, wood meal, starch and crystalline cellulose; synthetic or natural high molecular weight polymers, such as cumarone resins, petroleum resins, alkyd resins, polyvinyl chloride, polyalkylene glycols, ketone resins, ester gums, copal gum and dammar gum; waxes such as carnauba wax and beeswax; or urea.

Examples of suitable liquid carriers include:

paraffinic or naphthenic hydrocarbons, such as kerosene, mineral oil, spindle oil and white oil; aromatic hydrocarbons, such as benzene, toluene, xylene, ethylbenzene, cumene and methylnaphthalene; chlorinated hydrocarbons, such as carbon tetrachloride, chloroform, trichloroethylene, monochlorobenzene and o-chlorotoluene; ethers such as dioxane and tetrahydrofuran; ketones, such as acetone, methyl ethyl ketone, diisobutyl ketone, cyclohexanone, acetophenone and isophorone; esters such as ethyl acetate, amyl acetate, ethylene glycol acetate, diethylene glycol acetate, dibutyl maleate and diethyl succinate; alcohols such as methanol, n-hexanol, ethylene glycol, diethylene glycol, cyclohexanol, and benzyl alcohol; ether alcohols, such as ethylene glycol monoethyl ether, ethylene glycol phenyl ether, diethylene glycol ethyl ether and diethylene glycol butyl ether; other polar solvents, such as dimethylformamide or dimethyl sulphoxide; and water.

Suitable gaseous carriers include:

air, nitrogen, carbon dioxide and freon (Freon is a Trade Mark); they may be mixed in known manner to give a propellant.

The compositions of the invention may contain one or more surface active agents and/or polymers to improve the properties of the compositions and help them to disperse, emulsify, spread, penetrate and bind or to control disintegration, improve fluidity or impart corrosion resistance to the composition, or to stabilize the active compound. Any of the conventional classes of surface active agent, (non-ionic, anionic, cationic or amphoteric) may be employed, but it is preferred to employ non-ionic and/or anionic surface active agents whereby wetting, adhesion and absorption and desired effects may be improved.

Examples of suitable non-ionic surface active agents include:

the polymerization adducts of ethylene oxide with higher alcohols, such as lauryl alcohol, stearyl alcohol and oleyl alcohol; the polymerization adducts of ethylene oxide with alkylphenols, such as isooctoylphenol or nonoylphenol; the polymerization adducts of ethylene oxide with alkylnaphthols, such as butylnaphthol or octylnaphthol; the polymerization adducts of ethylene oxide with higher fatty acids, such as palmitic acid, stearic acid or oleic acid; the polymerization adducts of ethylene oxide with mono- or dialkylphosphoric acids, such as stearylphosphoric acid or dilaurylphosphoric acid; the polymerization adducts of ethylene oxide with amines, such as dodecylamine; the polymerization adducts of ethylene oxide with higher fatty amides, such as stearamide; higher fatty acid esters of polyhydric alcohols, such as sorbitan, and the polymerization adducts of ethylene oxide therewith; and the polymerization adducts of ethylene oxide with propylene oxide.

Examples of suitable anionic surface active agents include:

alkyl sulphate salts, such as sodium lauryl sulphate or oleyl suphate amine salt; alkyl sulphonate salts, such as sodium dioctyl sulphosuccinate or sodium 2-ethylhexenesulphonate; and aryl sulphonate salts, such as sodium isopropylnaphthalenesulphonate, sodium methylenebisnaphthalenesulphonate, sodium ligninsulphonate or sodium dodecylbenzenesulphonate.

Moreover, the compositions of the present invention may be used in combination with high molecular weight compounds or other formulation agents, such as casein, gelatin, albumin, glue, sodium alginate, carboxymethylcellulose, methylcellulose, hydroxyethylcellulose or polyvinyl alcohol, in order to improve the properties and/or to increase the biological effect of the compositions.

The above-mentioned carriers and various auxiliary agents may be used alone or in any desired combination, depending upon the type of preparation, the application and other factors.

For example, dusts may conveniently contain from 1 to 25% by weight of the active compound, the remainder being a solid carrier.

Wettable powders may conveniently contain, for example, from 25 to 90% by weight of the compound, the remainder being a solid carrier and a dispersing and wetting agent, if required, together with a protective colloidal agent, a thixotropic agent and an anti-foaming agent.

Granules may conveniently contain from 1 to 35% by weight of the active compound, a major portion of the remainder being a solid carrier. The active compound is homogeneously admixed with the solid carrier or is adhered or adsorbed onto the carrier surface; the diameter of each granule is preferably from 0.2 to 1.5 mm.

Emulsifiable concentrates may conveniently contain, for example, from 5 to 20% by weight of an emulsifying agent, the remainder being a liquid carrier, together with, if required, a corrosion inhibitor.

Oil preparations may conveniently contain from 0.5 to 5% by weight of the active compound, the remainder being a liquid carrier such as kerosene.

Aerosols may conveniently contain from 0.1 to 5% by weight of the active compound and optionally a perfume, the remainder being an oily and/or aqueous carrier, and a propellant such as liquified petroleum gas, freon or carbon dioxide.

The compositions of the invention may be applied, for example, to paddy or other fields before or after emergence of disease in plants or to plants and domestic animals bearing harmful insects and mites; concentration of 100–1,000 ppm for the active ingredient is usually suitable, especially for application to leaves and stems of plants, soil and animals, whereby effective control may be attained. The composition of the invention may conveniently be blended with other insecticides for a broader insecticidal spectrum and, in some case, a synergistic effect may be expected.

Suitable insecticides include:

phosphorus-containing insecticides; such as O,O-diethyl O-(2-isopropyl-4-methyl-6-pyrimidinyl)phosphorothioate, O,-O-diethyl S-2-[(ethylthio)ethyl]phosphorodithioate, O,O-dimethyl O-(3-methyl-4-nitrophenyl)thiophosphate, O,O-dimethyl S-(N-methylcarbamoylmethyl)phosphorodithioate, O,O-dimethyl S-(N-methyl-N-formylcarbamoylmethyl)phosphorodithioate, O,O-dimethyl S-2-(ethylthio)ethylphosphorodithioate, O,O-dimethyl-1-hydroxy-2,2,2-trichloroethylphosphonate, O,O-diethyl-O-(5-phenyl-3-isoxazolyl)-phosphorothioate, O,O-dimethyl-O-(3-methyl-4-methyl mercaptophenyl)thiophosphate, O-ethyl-O-p-cyanophenyl phenylphosphonothioate, O,O-dimethyl S-(1,2-dicarboethoxyethyl)phosphorodithioate, 2-chloro-1-(2,4,5-trichlorophenyl)vinyldimethyl phosphate, 2-chloro-1-(2,4-dichlorophenyl)vinyldimethyl phosphate, O,O-dimethyl O-p-cyanophenyl phosphorothioate, 2,2-dichlorovinyldimethylphosphate, ethyl mercaptophenylacetate, O,O-dimethyl phosphorodithioate, S-[(6-chloro-2-oxo-3-benzooxazolinyl)methyl-]O,O-diethylphosphorodithioate, 4-methylthiophenyl dipropylphosphate, 2-chloro-1-(2,4-dichlorophenyl)-vinyldiethylphosphate, O,O-diethyl-O-(3-oxo-2-phenyl-2H-pyridazin-6-yl)phosphorothioate, O,O-dimethyl S-(1-methyl-2-ethylsulphinyl)ethyl phosphorothioate, O,O-dimethyl S-phthalimidomethyl phosphorodithioate, dimethylmethylcarbamoylethylthioethyl thiophosphorothioate, O,O-diethyl S-(N-ethoxycarbonyl-N-methylcarbamoylmethyl)phosphorodithioate, O,O-dimethyl-S-[2-methoxy-1,3,4-thiadiazol-5(4H)-onyl-(4)-methyl]dithiophosphate, 2-methoxy-4H-1,3,2-benzodioxaphosphorin 2-sulphide, O,O-diethyl-O-(3,5,6-trichloro-2-pyridyl)phosphorothioate, O,S-dimethyl-N-acetyl phosphoroamidothioate, O-2,4-dichlorophenyl S-propylphosphorodithioate, O,O-diethyl S-(2-chloro- 1-phthalimidoethyl)phosphorodithioate and O-6-ethoxy-2-ethylpyrimidine-4-yl O,O-dimethylphosphorothioate;

carbamate-type insecticides; such as 1-naphthyl N-methyl-carbamate, S-methyl-N-[methylcarbamoyloxy]-thioacetoimidate, 2-sec-butylphenyl-N-methylcarbamate, 2-isopropoxyphenyl-N-methylcarbamate, 1,3-bis(carbamoylthio)-2-(N,N-dimethylamino)propane hydrochloride and 2-dimethylamino-5,6-dimethylpyrimidin-4-yl dimethyl carbamate;

and other insecticides; such as nicotine sulphate, milbemycin D, 6-methyl-2,3-quinoxalinedithiocyclic S,S-dithiocarbonate, 2,4-dinitro-6-sec-butylphenyldimethylacrylate, 1,1-bis(p-chlorophenyl)-2,2,2-trichloroethanol, azoxybenzene, di-(p-chlorophenyl)cyclopropyl carbinol, isopropyl 4,4-dichlorobenzylate, ethyl-4,4'-dichlorobenzylate, ethyl O-benzoyl-3-chloro-2,6-dimethoxybenzohydroxymate, isopropyl 4,4'-dibromobenzylate, tricyclohexyltin hydroxide, 2-(4-t-butylphenoxy)cyclohexylpropinylsulphide, 3-methyl-1,5-bis(2,4-xylyl)-1,3,5-triazapenta-1,4-diene, 2,4,5,4'-tetrachlorodiphenylsulphone, hexachlorohexahydromethanobenzodioxathiepineoxide, 5-dimethylamino-1,2,3-trithiane hydrogenoxalate and machine oil.

However, the nature of any such additional insecticide is not critical.

The composition of the invention may be blended with fungicides. Suitable fungicides are as follows.

Carbamate-type fungicides; such as 3,3'-ethylenebis(-tetrahydro-4,6,dimethyl-2H-1,3,5-thiadiazine-2-thione, zinc or manganese ethylenebisdithiocarbamate, bis(-dimethyldithiocarbamoyl)disulphide, zinc propylenebisdithiocarbamate, methyl 1-(butylcarbamoyl)-2-benzimidazolcarbamate, 1,2-bis(3-methoxycarbonyl-2-thioureido)benzene and bisdimethyldithiocarbamoyl zinc ethylenebisdithiocarbamate;

dicarboximide-type fungicides, such as N-trichloromethylthio-4-cyclohexene-1,2-dicarboximide and N-tetrachloroethylthio-4-cyclohexene-1,2-dicarboximide;

oxazine-type fungicides, such as 5,6-dihydro-2-methyl-1,4-oxazine-3-carboxanilide-4,4-dioxide; naphthoquinone-type fungicides, such as 2,3-dichloro-1,4-naphthoquinone;

and other fungicides, such as 3-hydroxy-5-methylisoxazole, 5-ethoxy-3-trichloromethyl-1,2,4-thiadiazole, 2,4-dichloro-6-(o-chloroanilino)-1,3,5-triazine, 2,3-dicyano-1,4-dithioanthraquinone, copper 8-quinolate, polyoxin, validamycin, tetrachloroisophthalonitrile, 2-(1-methylpropyl)-4,6-dinitrophenol $\beta,\beta$-dimethylacrylate, triphenyltin hydroxide, phytomycin, dinitromethylheptylphenyl crotonate, 5-butyl-2-dimethylamino-6-methylpyrimidine-4-ol, 6-(3,5-dichloro-4-methylphenyl)-3-(2H)pyridazinone, 6-(3-bromophenyl)-3-(2H)pyridazinone, N-(2,6-dimethylphenyl)-N-methoxyacetylanine methyl ester and bis(8-quadinooctyl)amine acetate.

Examples of formulations of compositions according to the invention will be given below, in which parts are all by weight:

FORMULATION EXAMPLE 1

Dust 5 parts of Compound No 311, 50 parts of talc and 45 parts of kaolin were uniformly mixed to form a dust.

In a similar manner a like composition was prepared based on compound number 42

FORMULATION EXAMPLE 2

Wettable Powder 50 parts of Compound No 312, 29 parts of clay, 10 parts of diatomaceous earth, 5 parts of white carbon, 3 parts of sodium ligninsulphonate, 2 parts of "Newcol" 1106 (a trade name of Nihon Nyukazai K K) and 1 part of polyvinyl alcohol were uniformly mixed in a mixer and then pulverized three times by a hammer mill to give a wettable powder.

In a similar manner a like composition was prepared based on compound number 50

FORMULATION EXAMPLE 3

Granules 70 parts of Compound No 329 were finely pulverized, and 30 parts of clay were added thereto and then mixed in a mixer to form a premix. 10 parts of this premix were uniformly mixed with 60 parts of clay and 30 parts of bentonite in a mixer. The mixture was then kneaded with a suitable amount of water in a kneader, extruded through a screen with holes having a diameter of 0.8 mm and dried in a draught drier at 50° C. The product thus formed was adjusted by a sifter to form granules.

In a similar manner a like composition was prepared based on compound number 54

FORMULATION EXAMPLE 4

Emulsifiable Concentrate 20 parts of Compound No 352 were mixed with 10 parts of "Sorpol" SM-200 (a trade name of Toho Kagaku K K) and 70 parts of xylol, and the mixture was thoroughly blended to give an emulsifiable concentrate.

In a similar manner a like composition was prepared based on compound number 54

The present invention is further illustrated by the following Application Examples. Wettable powders prepared according to the procedures of Formulation Example 2 were used, each containing 50% by weight of the active compound of this invention.

APPLICATION EXAMPLE 1

Activity against the adult two-spotted spider mite

Test suspensions containing 300 ppm of each of the active compounds according to the invention and 0.01% of a spreader were prepared. Leaves of the cowpea (*Vigna sinensis*) bearing adult two-spotted spider mites (*Tetranychus urticae*) were dipped for 10 seconds into each suspension. After air-drying, the leaves were allowed to stand in a room maintained at 25° C. Each test group contained 50 mites on average.

A mortality of 100% after 72 hours was taken as 4, and 99–80% mortality after 72 hours taken as 3. The results are shown in Table 1.

TABLE 1

| compound number | acaracidal effect | compound number | acaracidal effect |
|---|---|---|---|
| 4 | 3 | 44 | 4 |
| 5 | 4 | 45 | 4 |
| 7 | 4 | 48 | 4 |
| 12 | 4 | 49 | 4 |
| 13 | 4 | 50 | 4 |
| 14 | 3 | 51 | 4 |
| 15 | 4 | 52 | 4 |
| 16 | 4 | 53 | 4 |

TABLE 1-continued

| compound number | acaracidal effect | compound number | acaracidal effect |
|---|---|---|---|
| 17 | 4 | 54 | 4 |
| 18 | 4 | 55 | 4 |
| 19 | 4 | 56 | 4 |
| 20 | 4 | 57 | 4 |
| 22 | 3 | 58 | 4 |
| 23 | 4 | 59 | 4 |
| 25 | 4 | 60 | 4 |
| 27 | 3 | 61 | 4 |
| 62 | 4 | 63 | 4 |
| 29 | 3 | 64 | 4 |
| 30 | 4 | 65 | 4 |
| 39 | 4 | 66 | 4 |
| 40 | 4 | 67 | 4 |
| 41 | 4 | 68 | 4 |
| 42 | 4 | 69 | 4 |
| 43 | 4 | 70 | 3 |
| 71 | 4 | 101 | 4 |
| 72 | 3 | 102 | 4 |
| 74 | 4 | 103 | 4 |
| 78 | 4 | 104 | 4 |
| 79 | 4 | 105 | 3 |
| 80 | 4 | 106 | 4 |
| 81 | 4 | 107 | 4 |
| 82 | 4 | 108 | 4 |
| 84 | 4 | 109 | 3 |
| 85 | 4 | 126 | 3 |
| 86 | 4 | 127 | 4 |
| 87 | 4 | 129 | 4 |
| 88 | 4 | 130 | 4 |
| 89 | 4 | 132 | 4 |
| 90 | 4 | 133 | 3 |
| 91 | 4 | 148 | 4 |
| 92 | 4 | 166 | 4 |
| 93 | 4 | 167 | 4 |
| 94 | 4 | 168 | 3 |
| 95 | 4 | 170 | 4 |
| 96 | 4 | 171 | 4 |
| 97 | 4 | 172 | 4 |
| 98 | 4 | 175 | 3 |
| 99 | 4 | 176 | 4 |
| 100 | 4 | 177 | 4 |
| 178 | 3 | 239 | 4 |
| 179 | 3 | 240 | 4 |
| 180 | 4 | 241 | 4 |
| 181 | 4 | 242 | 4 |
| 182 | 4 | 243 | 4 |
| 183 | 4 | 244 | 4 |
| 185 | 4 | 246 | 4 |
| 189 | 4 | 247 | 4 |
| 191 | 3 | 253 | 4 |
| 196 | 4 | 256 | 4 |
| 197 | 4 | 258 | 4 |
| 199 | 4 | 259 | 4 |
| 200 | 4 | 260 | 4 |
| 203 | 4 | 261 | 4 |
| 204 | 4 | 262 | 4 |
| 205 | 3 | 264 | 4 |
| 206 | 4 | 265 | 4 |
| 207 | 4 | 276 | 3 |
| 208 | 4 | 277 | 4 |
| 217 | 4 | 278 | 4 |
| 218 | 3 | 279 | 3 |
| 220 | 4 | 280 | 4 |
| 221 | 3 | 281 | 4 |
| 229 | 4 | 282 | 4 |
| 236 | 3 | 283 | 4 |
| 238 | 4 | 284 | 4 |
| 286 | 3 | 315 | 4 |
| 287 | 4 | 316 | 4 |
| 288 | 4 | 317 | 3 |
| 289 | 4 | 318 | 4 |
| 291 | 4 | 320 | 4 |
| 301 | 3 | 326 | 3 |
| 302 | 4 | 336 | 3 |
| 303 | 3 | 373 | 3 |
| 304 | 4 | 381 | 4 |
| 305 | 4 | 382 | 3 |
| 307 | 4 | 383 | 3 |
| 311 | 4 | 385 | 4 |
| 314 | 3 | 387 | 4 |

TABLE 1-continued

| compound number | acaracidal effect | compound number | acaracidal effect |
|---|---|---|---|
| 388 | 4 | | |

APPLICATION EXAMPLE 2

Ovicidal activity against the two-spotted spider mite

Test suspensions containing 300 ppm of each active compound were prepared as in Application Example 1. Leaves of the cowpea bearing eggs of the two-spotted spider mites were dipped for 10 seconds into each suspension. After air-drying, the leaves were allowed to stand in a room maintained at 25° C.

A 100% ovicidal activity after 2 weeks was taken as 4, and 99–80% ovicidal activity after 2 weeks as 3. The results are shown in Table 2.

TABLE 2

| compound number | ovicidal effect | compound number | ovicidal effect |
|---|---|---|---|
| 11 | 3 | 50 | 4 |
| 12 | 4 | 51 | 4 |
| 13 | 4 | 52 | 4 |
| 14 | 3 | 53 | 4 |
| 15 | 4 | 54 | 4 |
| 16 | 4 | 55 | 4 |
| 17 | 4 | 56 | 4 |
| 18 | 4 | 57 | 4 |
| 19 | 4 | 58 | 4 |
| 20 | 4 | 59 | 4 |
| 23 | 3 | 60 | 4 |
| 25 | 4 | 61 | 4 |
| 26 | 4 | 62 | 4 |
| 27 | 4 | 63 | 4 |
| 29 | 3 | 64 | 3 |
| 30 | 4 | 66 | 4 |
| 39 | 3 | 67 | 4 |
| 40 | 4 | 68 | 4 |
| 41 | 4 | 69 | 4 |
| 42 | 4 | 70 | 4 |
| 43 | 4 | 71 | 4 |
| 45 | 4 | 72 | 4 |
| 48 | 4 | 74 | 4 |
| 49 | 4 | 79 | 4 |
| 80 | 3 | 108 | 4 |
| 81 | 3 | 109 | 3 |
| 82 | 4 | 122 | 3 |
| 84 | 4 | 127 | 4 |
| 85 | 4 | 129 | 4 |
| 86 | 4 | 130 | 4 |
| 87 | 4 | 132 | 4 |
| 88 | 4 | 133 | 3 |
| 89 | 4 | 148 | 3 |
| 90 | 4 | 166 | 4 |
| 91 | 4 | 167 | 4 |
| 92 | 4 | 168 | 4 |
| 93 | 4 | 170 | 4 |
| 94 | 4 | 171 | 4 |
| 95 | 4 | 172 | 4 |
| 96 | 4 | 175 | 4 |
| 97 | 4 | 176 | 4 |
| 98 | 4 | 177 | 4 |
| 99 | 4 | 178 | 3 |
| 100 | 4 | 179 | 4 |
| 101 | 3 | 180 | 4 |
| 103 | 4 | 181 | 4 |
| 104 | 4 | 182 | 3 |
| 105 | 4 | 183 | 4 |
| 106 | 4 | 185 | 4 |
| 107 | 4 | | |
| 196 | 4 | 258 | 4 |
| 197 | 4 | 259 | 4 |
| 199 | 4 | 260 | 4 |
| 200 | 4 | 261 | 4 |
| 203 | 4 | 262 | 4 |
| 204 | 4 | 264 | 4 |
| 205 | 4 | 265 | 4 |

TABLE 2-continued

| compound number | ovicidal effect | compound number | ovicidal effect |
| --- | --- | --- | --- |
| 206 | 4 | 276 | 3 |
| 207 | 4 | 277 | 4 |
| 208 | 3 | 278 | 4 |
| 217 | 4 | 279 | 4 |
| 218 | 3 | 280 | 4 |
| 220 | 4 | 281 | 4 |
| 229 | 4 | 282 | 4 |
| 238 | 4 | 283 | 4 |
| 239 | 4 | 284 | 4 |
| 240 | 4 | 286 | 4 |
| 241 | 4 | 287 | 4 |
| 242 | 4 | 288 | 3 |
| 243 | 4 | 289 | 4 |
| 244 | 4 | 291 | 4 |
| 246 | 4 | 300 | 3 |
| 247 | 4 | 302 | 4 |
| 253 | 4 | 304 | 4 |
| 255 | 3 | 305 | 4 |
| 256 | 3 | 307 | 3 |
| 316 | 4 | 326 | 3 |
| 318 | 4 | 336 | 3 |
| 325 | 3 | 373 | 3 |

APPLICATION EXAMPLE 3

Activity against the final instar larvae of diamondback moth

Radish leaves were dipped for 30 seconds into test suspensions containing 500 ppm of each of the active compounds according to the invention. The leaves were then air-dried and each leaf was placed into a plastic cup having a diameter of 8 cm. 10 final instar larvae of the diamondback moth (*Plutella xylosella*) were released into each cup, and the emergence inhibition rate after 120 hours was assessed. The tests were conducted in duplicate, and the results are shown in Table 3.

TABLE 3

| compound number | inhibition rate (%) | compound number | inhibition rate (%) |
| --- | --- | --- | --- |
| 6 | 70 | 71 | 90 |
| 7 | 60 | 72 | 100 |
| 13 | 100 | 82 | 70 |
| 14 | 80 | 86 | 90 |
| 15 | 80 | 87 | 100 |
| 16 | 90 | 88 | 80 |
| 19 | 60 | 89 | 100 |
| 40 | 60 | 91 | 100 |
| 41 | 70 | 92 | 70 |
| 42 | 90 | 95 | 90 |
| 43 | 80 | 97 | 100 |
| 44 | 60 | 103 | 70 |
| 48 | 90 | 129 | 90 |
| 50 | 90 | 130 | 90 |
| 51 | 70 | 131 | 90 |
| 52 | 100 | 132 | 70 |
| 53 | 100 | 236 | 90 |
| 54 | 100 | 238 | 90 |
| 55 | 60 | 239 | 100 |
| 58 | 100 | 240 | 80 |
| 60 | 90 | 242 | 80 |
| 63 | 60 | 243 | 100 |
| 66 | 80 | 244 | 90 |
| 69 | 80 | 246 | 90 |
| 70 | 100 | 247 | 80 |
| 291 | 80 | 314 | 100 |
| 300 | 100 | 316 | 100 |
| 301 | 90 | 317 | 90 |
| 303 | 80 | 325 | 80 |
| 307 | 70 | 326 | 80 |
| 308 | 100 | 372 | 100 |

APPLICATION EXAMPLE 4

Activity against the green peach aphid

Test suspension containing 100 ppm of each of the active compounds were sprayed onto leaves of a cabbage bearing the green peach aphid (*Myzus persicae*) at the rate of 10 ml per leaf.

Each leaf was placed by its leafstalk in a 30 ml bottle containing water and the mouth of the bottle was plugged with cotton wool.

The bottles were then left in a room maintained at 25° C. After 72 hours, the percentage mortality of the aphids was assessed. The results are shown in Table 4.

TABLE 4

| compound number | mortality (%) | compound number | mortality (%) |
| --- | --- | --- | --- |
| 11 | 56 | 86 | 90 |
| 13 | 86 | 87 | 100 |
| 15 | 60 | 89 | 100 |
| 16 | 100 | 91 | 100 |
| 17 | 60 | 92 | 98 |
| 18 | 60 | 95 | 100 |
| 19 | 100 | 97 | 100 |
| 20 | 60 | 98 | 75 |
| 23 | 50 | 106 | 90 |
| 27 | 90 | 107 | 90 |
| 48 | 88 | 108 | 95 |
| 49 | 95 | 129 | 86 |
| 50 | 100 | 130 | 100 |
| 52 | 100 | 133 | 100 |
| 54 | 100 | 168 | 60 |
| 55 | 93 | 172 | 70 |
| 58 | 50 | 177 | 85 |
| 60 | 100 | 180 | 90 |
| 61 | 100 | 183 | 96 |
| 63 | 100 | 189 | 100 |
| 66 | 45 | 196 | 100 |
| 68 | 87 | 197 | 100 |
| 69 | 98 | 199 | 100 |
| 70 | 100 | 200 | 100 |
| 71 | 96 | 207 | 85 |
| 72 | 98 | 218 | 50 |
| 229 | 100 | 258 | 80 |
| 230 | 85 | 259 | 90 |
| 238 | 100 | 260 | 80 |
| 239 | 100 | 262 | 85 |
| 240 | 100 | 264 | 90 |
| 241 | 60 | 265 | 85 |
| 242 | 100 | 276 | 80 |
| 243 | 100 | 279 | 90 |
| 244 | 100 | 281 | 90 |
| 245 | 100 | 282 | 80 |
| 247 | 100 | 283 | 80 |

APPLICATION EXAMPLE 5

Activity against powdery mildew in cucumbers

Cucumber seedlings (variety Sagamihanjiro) were planted two per 12 cm diameter pot and used as host plants when the first leaf was fully grown and open. Each test group of three pots was treated with each of the active compounds by spraying on an aqueous suspension containing 500 ppm of the active compound at the rate of 30 ml per 3 pots.

After air-drying, the host plants were inoculated with *Sphaerotheca fuliginea* by brushing the microorganism from already infected cucumber leaves with a brush and letting the microorganism fall onto the host plants. The host plants were then kept in a greenhouse at 24°–26° C. for 10 days, and at the end of this period the percentage diseased area was measured. Each test was conducted in triplicate, and the average results are shown in Table 5.

TABLE 5

| compound number | diseased area (%) | compound number | diseased area (%) |
| --- | --- | --- | --- |
| 3 | 0 | 161 | 6 |
| 5 | 0 | 162 | 0 |
| 6 | 4 | 167 | 3 |
| 7 | 3 | 182 | 0 |
| 13 | 0 | 183 | 6 |
| 38 | 6 | 190 | 3 |
| 39 | 0 | 191 | 2 |
| 42 | 3 | 192 | 6 |
| 43 | 6 | 193 | 4 |
| 44 | 0 | 196 | 5 |
| 45 | 7 | 203 | 8 |
| 47 | 3 | 205 | 6 |
| 48 | 5 | 206 | 7 |
| 49 | 8 | 207 | 9 |
| 50 | 7 | 208 | 2 |
| 51 | 4 | 209 | 1 |
| 54 | 2 | 210 | 2 |
| 66 | 6 | 216 | 8 |
| 68 | 2 | 218 | 1 |
| 69 | 1 | 219 | 2 |
| 70 | 4 | 222 | 5 |
| 78 | 5 | 223 | 2 |
| 79 | 5 | 235 | 0 |
| 80 | 9 | 236 | 4 |
| 81 | 2 | 238 | 1 |
| 82 | 0 | 239 | 2 |
| 83 | 3 | 240 | 3 |
| 85 | 1 | 241 | 1 |
| 86 | 8 | 242 | 3 |
| 87 | 7 | 243 | 6 |
| 88 | 4 | 244 | 5 |
| 89 | 2 | 247 | 3 |
| 95 | 4 | 285 | 4 |
| 103 | 5 | 289 | 5 |
| 104 | 6 | 301 | 0 |
| 105 | 6 | 302 | 2 |
| 106 | 4 | 303 | 4 |
| 109 | 9 | 304 | 0 |
| 110 | 8 | 305 | 4 |
| 111 | 3 | 306 | 8 |
| 112 | 9 | 307 | 0 |
| 113 | 2 | 314 | 9 |
| 115 | 6 | 316 | 6 |
| 116 | 2 | 317 | 0 |
| 119 | 4 | 320 | 9 |
| 121 | 8 | 325 | 1 |
| 122 | 2 | 326 | 9 |
| 125 | 4 | 327 | 2 |
| 126 | 4 | 328 | 0 |
| 128 | 8 | 329 | 3 |
| 130 | 9 | 330 | 8 |
| 131 | 2 | 331 | 4 |
| 135 | 6 | 332 | 0 |
| 137 | 1 | 338 | 7 |
| 138 | 9 | 344 | 4 |
| 140 | 2 | 348 | 6 |
| 141 | 0 | 349 | 8 |
| 142 | 3 | 350 | 0 |
| 143 | 8 | 351 | 1 |
| 144 | 3 | 353 | 5 |
| 145 | 4 | 358 | 2 |
| 147 | 0 | 364 | 0 |
| 150 | 7 | 368 | 3 |
| 151 | 6 | 369 | 6 |
| 152 | 8 | 370 | 0 |
| 153 | 0 | 384 | 4 |
| 155 | 1 | 386 | 2 |
| 156 | 5 | Control (None) | 100 |
| 158 | 3 | | |

APPLICATION EXAMPLE 6

Activity against the anthracnose in cucumbers

Cucumber seedlings (variety Sagamihanjiro) were planted two per 12 cm diameter pot and used as host plants when the first leaf was fully grown and open. Each test group of three pots was treated with each of the active compounds by spraying on an aqueous suspension containing 500 ppm of the active compound at the rate of 30 ml per 3 pots.

After air-drying, the host plants were incoculated by spraying with a spore suspension of *Collectotrichum lagenarium* and kept in a wet room for 24 hours at 20°-22° C. and 100% relative humidity. The pots were then placed in a greenhouse at 26° C. and, 7 days after the inoculation, the percentage diseased area of the cotyledon and the first leaf was culculated. The results are shown in Table 6.

TABLE 6

| compound number | diseased area (%) | compound number | diseased area (%) |
| --- | --- | --- | --- |
| 1 | 0 | 222 | 9 |
| 2 | 0 | 225 | 5 |
| 11 | 7 | 227 | 8 |
| 12 | 8 | 232 | 4 |
| 13 | 3 | 289 | 2 |
| 14 | 5 | 299 | 7 |
| 16 | 8 | 300 | 2 |
| 19 | 7 | 309 | 2 |
| 24 | 4 | 314 | 0 |
| 25 | 2 | 315 | 1 |
| 49 | 0 | 319 | 1 |
| 50 | 1 | 320 | 5 |
| 54 | 5 | 325 | 1 |
| 58 | 0 | 326 | 4 |
| 68 | 2 | 329 | 4 |
| 85 | 0 | 330 | 0 |
| 103 | 7 | 347 | 2 |
| 105 | 4 | 348 | 8 |
| 110 | 8 | 351 | 8 |
| 121 | 5 | 354 | 0 |
| 143 | 9 | 365 | 5 |
| 147 | 5 | 366 | 7 |
| 149 | 3 | 384 | 3 |
| 155 | 8 | 386 | 4 |
| 208 | 4 | Control (None) | 96 |
| 209 | 3 | | |

APPLICATION EXAMPLE 7

Activity against early blight in tomatoes

Groups of two tomato plants (Variety Shinfukuju) per pot were planted in pots having a diameter of 12 cm and used as host plants when at the 5 to 6 leaf stage. Each pot was treated with 30 ml of an aqueous suspension containing 500 ppm of each of the active compounds by spraying over the stems and leaves. After air-drying, each plant was inoculated with a spore suspension of *Alternaria solani* and kept in a wet room for 24 hours at 20°-22° C. and 100% relative humidity. The pots were then placed in a greenhouse at 24°-26° C. for 3 days. The presence of the disease on all leaves was investigated and the number of diseased spots per leaf was calculated, using three pots for each compound. The results are shown in Table 7.

TABLE 7

| compound number | diseased spots | compound number | diseased spots |
| --- | --- | --- | --- |
| 3 | 8 | 85 | 5 |
| 6 | 8 | 103 | 8 |
| 12 | 0 | 111 | 4 |
| 17 | 3 | 123 | 6 |
| 24 | 6 | 156 | 3 |
| 30 | 2 | 196 | 4 |
| 33 | 5 | 203 | 6 |
| 36 | 5 | 212 | 5 |
| 38 | 7 | 217 | 2 |

TABLE 7-continued

| compound number | diseased spots | compound number | diseased spots |
|---|---|---|---|
| 42 | 7 | 224 | 7 |
| 43 | 8 | 317 | 6 |
| 45 | 9 | 318 | 0 |
| 48 | 4 | 341 | 1 |
| 49 | 9 | 359 | 1 |
| 60 | 7 | 363 | 1 |
| 74 | 3 | Control (None) | 48 |
| 80 | 5 | | |

APPLICATION EXAMPLE 8

Activity against late blight in tomatoes

Groups of tomatoes (Variety Shinfukuju) at the 5 to 6 leaf stage, 1 plant per pot, were sprayed with 20 ml per pot of an aqueous suspension containing 500 ppm of each of the active compounds. After air-drying, each plant was inoculated with a spore suspension of *Phytophthora infestans* by spraying, and then kept in a wet room for 24 hours at 20° C. and more than 95% relative humidity. The pots were then kept in a greenhouse at 25° C., and, after 5 days, the diseased area of the upper three leaves of each plant was measured. Two pots were used for each test and the average diseased area per leaf was calculated. The results are shown in Table 8.

TABLE 8

| compound number | diseased area (%) | compound number | diseased area (%) |
|---|---|---|---|
| 2 | 0 | 113 | 2 |
| 3 | 3 | 167 | 1 |
| 9 | 9 | 185 | 0 |
| 14 | 1 | 196 | 3 |
| 16 | 1 | 197 | 7 |
| 17 | 3 | 199 | 2 |
| 19 | 8 | 200 | 8 |
| 23 | 7 | 220 | 2 |
| 24 | 1 | 226 | 0 |
| 27 | 5 | 229 | 6 |
| 30 | 0 | 238 | 2 |
| 38 | 7 | 291 | 4 |
| 39 | 5 | 338 | 5 |
| 40 | 3 | 339 | 3 |
| 48 | 9 | 344 | 0 |
| 53 | 4 | 346 | 9 |
| 56 | 8 | 351 | 0 |
| 90 | 4 | 358 | 6 |
| 93 | 0 | 375 | 4 |
| 110 | 6 | Control (None) | 100 |
| 111 | 4 | | |

APPLICATION EXAMPLE 9

Activity against rice blast

Rice plant seedlings (variety Nohrin No 20) at the 4 to 5 leaf stage were sprayed with an aqueous suspension containing 500 ppm of each of the active compounds at the rate of 30 ml per 2 pots. After 3 days, the host plants were inoculated with *Piricularia oryzae* by spraying as a spore suspension, and the host plants were kept in a wet room for 48 hours at 20°–22° C. and 100% relative humidity. The host plants were then placed in a greenhouse at 24°–26° C. and, after 3 days, the number of diseased spots on the upper two leaves was counted. Each test was conducted in triplicate, and the mean number of diseased spots per leaf was measured. The results are shown in Table 9.

TABLE 9

| compound number | diseased spots | compound number | diseased spots |
|---|---|---|---|
| 31 | 1.8 | 301 | 1.0 |
| 32 | 1.7 | 315 | 1.4 |
| 33 | 1.5 | 316 | 1.1 |
| 79 | 1.0 | 319 | 1.0 |
| 81 | 1.2 | 323 | 1.7 |
| 82 | 1.0 | 324 | 1.8 |
| 84 | 1.3 | 325 | 1.0 |
| 86 | 1.0 | 336 | 1.3 |
| 88 | 1.2 | 353 | 1.4 |
| 142 | 1.0 | 358 | 1.0 |
| 155 | 1.0 | 360 | 1.0 |
| 182 | 1.1 | 363 | 1.4 |
| 193 | 1.0 | 365 | 1.7 |
| 235 | 1.4 | 386 | 1.2 |
| 285 | 1.6 | Control (None) | 43.4 |

APPLICATION EXAMPLE 10

Activity against damping-off in cucumbers

A microorganism causing damping-off in cucumbers (*Fusarium oxysporum*) that had been cultured on rice bran at 28° C. for 2 weeks was thoroughly blended with soil, which was put into pots of diameter 12 cm. Seeds of cucumber (variety Sagamihanjiro) were sown on the pots, 20 per pot, and suspensions containing 500 ppm of each of the active compounds were poured onto respective pots at the rate of 3 l/m². The pots were then maintained in a greenhouse at 25° C. for 2 weeks and the number of diseased seedlings was determined, using 3 pots per test group.

The results, which are the sum of 3 pots, are shown in Table 10.

TABLE 10

| compound number | diseased seedlings | compound number | diseased seedlings |
|---|---|---|---|
| 300 | 3 | 338 | 1 |
| 305 | 9 | 348 | 0 |
| 314 | 0 | 358 | 0 |
| 317 | 8 | 375 | 5 |
| 325 | 0 | 377 | 0 |
| 326 | 1 | 378 | 7 |
| 329 | 0 | 379 | 1 |
| 336 | 0 | 386 | 1 |
| Control (None) | 57 | | |

APPLICATION EXAMPLE 11

Activity against Fusarium wilt in tomatoes

Conidia of *Fusarium oxysporum* f. sp. lycopersici that had been cultured in a liquid medium were thoroughly blended with soil to give a soil contaminated with the microorganism. Wettable powders containing each of the active compounds were blended with the soil so that each active compound was present in an amount of 40 ppm based on the soil. The soil was put into plastic pots of 8×20 cm, and seedlings of tomato plant (variety Shinfukuju No 2) were transplanted, 2 per pot, four weeks after sowing. The pots were kept in a greenhouse at 25° C. for 3 weeks, then the number of diseased leaves was determined, using 3 pots per test group. The average result is indicated in Table 11.

TABLE 11

| compound number | diseased leaves | compound number | diseased leaves |
|---|---|---|---|
| 324 | 3.0 | 338 | 0.0 |
| 325 | 0.0 | 348 | 0.0 |

TABLE 11-continued

| compound number | diseased leaves | compound number | diseased leaves |
|---|---|---|---|
| 326 | 0.0 | 352 | 0.8 |
| 329 | 0.0 | 358 | 0.0 |
| 331 | 0.5 | 367 | 0.0 |
| 333 | 0.8 | 379 | 0.0 |
| 336 | 0.0 | 386 | 0.0 |
| Control (None) | 8.5 | | |

APPLICATION EXAMPLE 12

Activity against root rot in kidney beans

A microorganism causing root rot in kidney beans (*Fusarium solani* f. sp. phaseoli) that had been cultured or rice bran, sterilized with an autoclave, at 28° C. for 2 weeks was thoroughly blended with soil. The soil was put into plastic pots of 8×20 cm. Wettable powders containing 10% of each of active compounds were prepared and wet-coated onto seeds of kidney bean (variety Masterpiece) so that the active compound was present in an amount of 0.2% based on the weight of the seeds. The seeds were sown in the pots, 10 per pot, which were kept in a greenhouse for 3 weeks at 25° C. At the end of that period, the number of seedlings that had turned to brown at their lowest stem by infection with root rot was determined.

Each test group consisted of 6 pots, and the average number of diseased seedlings are indicated in Table 12.

TABLE 12

| compound number | diseased seedlings | compound number | diseased seedlings |
|---|---|---|---|
| 324 | 3.7 | 364 | 0.0 |
| 325 | 0.0 | 374 | 1.5 |
| 326 | 0.0 | 377 | 0 0 |
| 336 | 0.2 | 378 | 1.0 |
| 348 | 0.8 | Control (None) | 7.8 |

What is claimed is:

1. A fungicidal, insecticidal or acaricidal composition comprising an effective amount of a compound having the formula (I)

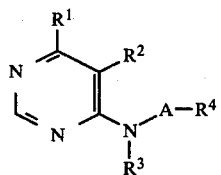

wherein:
$R^1$ and $R^2$ are the same or different and are each selected from the group consisting of alkyl groups having from 1 to 6 carbon atoms and halogen atoms, or $R^1$ and $R^2$ jointly represent a trimethylene or tetramethylene group;
$R^3$ is selected from the group consisting of a hydrogen atom and alkyl groups having from 1 to 6 carbon atoms;
A is an alkylene group; and
$R^4$ is selected from the group consisting of:
an unsubstituted phenyloxy group,
a substituted phenyloxy group substituted with at least one substituent selected from the group consisting of alkyl groups, halogen atoms, alkoxy groups having from 1 to 6 carbon atoms, alkylthio groups having from 1 to 6 carbon atoms, alkenyl groups having from 2 to 6 carbon atoms, a trifluoromethyl group and a nitro group,
an unsubstituted benzyloxy group,
a substituted benzyloxy group substituted in the phenyl ring with at least one substituent selected from the group consisting of alkyl groups, halogen atoms, alkoxy groups having from 1 to 6 carbon atoms, alkylthio groups having from 1 to 6 carbon atoms, alkenyl groups having from 2 to 6 carbon atoms, a trifluoromethyl group and a nitro group,
an unsubstituted phenyl group,
a substituted phenyl group substituted with one or two substituents selected from the group consisting of halogen atoms, alkyl groups having from 1 to 6 carbon atoms and alkoxy groups having from 1 to 6 carbon atoms,
a furyl group, and
a thienyl group
or a salt thereof, together with a carrier.

2. The composition of claim 1 wherein in said compound of the formula (I), $R^4$ is a group —$OR^5$ which is one of said unsubstituted phenyloxy, substituted phenyloxy, unsubstituted benzyloxy, and substituted benzyloxy groups; and acid addition salts thereof.

3. The composition of claim 2 wherein in said compound of the formula (I), $R^1$ and $R^2$ are each selected from the group consisting of alkyl groups having from 1 to 4 carbon atoms and halogen atoms, or $R^1$ and $R^2$ jointly represent a trimethylene or tetramethylene group; $R^3$ is selected from the group consisting of a hydrogen atom and alkyl groups having from 1 to 4 carbon atoms; A is an alkylene group having from 1 to 5 carbon atoms; and $R^5$ is selected from the group consisting of an unsubstituted phenyl group, and a substituted phenyl group substituted with one, two or three substituents selected from the group consisting of alkyl groups having from 1 to 10 carbon atoms, halogen atoms, alkoxy groups having from 1 to 4 carbon atoms, alkylthio groups having from 1 to 4 carbon atoms, alkenyl groups having from 3 to 4 carbon atoms, a trifluoromethyl group and a nitro group; and acid addition salts thereof.

4. The composition of claim 3 wherein in said compound of the formula (I), $R^1$ and $R^2$ are each methyl groups; and acid addition salts thereof.

5. The composition of claim 3 wherein in said compound of the formula (I), $R^1$ is an alkyl group having from 1 to 4 carbon atoms and $R^2$ is selected from the group consisting of chlorine and bromine atoms; and acid addition salts thereof.

6. The composition of claim 5 wherein in said compound of the formula (I), $R^1$ is a methyl group; and acid addition salts thereof.

7. The composition of claim 3 wherein in said compound of the formula (I), $R^1$ is selected from the group consisting of chlorine and bromine atoms and $R^2$ is an alkyl group having from 1 to 4 carbon atoms; and acid addition salts thereof.

8. The composition of claim 3 wherein in said compound of the formula (I), $R^3$ is a hydrogen atom; and acid addition salts thereof.

9. The composition of claim 3 wherein in said compound of the formula (I), A is an alkylene group having from 2 to 4 carbon atoms; and acid addition salts thereof.

10. The composition of claim 9 wherein in said compound of the formula (I), A is an ethylene group; and acid addition salts thereof.

11. The composition of claim 3 wherein in said compound of the formula (I), $R^5$ is a substituted phenyl group substituted with one or two alkyl groups having from 1 to 10 carbon atoms or with one alkyl group having from 1 to 10 carbon atoms and with one allyl group; and acid addition salts thereof.

12. The composition of claim 3 wherein in said compound of the formula (I), $R^5$ is a phenyl group substituted at the 2-position with an alkyl group having from 1 to 4 carbon atoms; and acid addition salts thereof.

13. The composition of claim 3 wherein in said compound of the formula (I), $R^5$ is a phenyl group substituted at the 2-position with a methyl or ethyl group and at the 4- or 5-position with an alkyl group having from 1 to 10 carbon atoms; and acid addition salts thereof.

14. The composition of claim 3 wherein in said compound of the formula (I), $R^5$ is a phenyl group substituted at the 2-position with a methyl group, at the 4- or 5-position with an alkyl group having from 1 to 10 carbon atoms and at the 6-position with a methyl group or a halogen atom; and acid addition salts thereof.

15. The composition of claim 5 or 6 wherein in said compound of the formula (I), $R^3$ is a hydrogen atom; A is an ethylene group; and $R^5$ is a phenyl group substituted at the 2-position with an alkyl group having from 1 to 4 carbon atoms; a phenyl group substituted at the 2-position with a methyl or ethyl and at the 4- or 5-position with an alkyl group having from 1 to 10 carbon atoms or with an allyl group; or a phenyl group substituted at the 2-position with a methyl group, at the 4-position with an alkyl group having from 1 to 10 carbon atoms and at the 6-position with a methyl group or a halogen atom; and acid addition salts thereof.

16. The composition of claim 3 wherein in said compound of the formula (I), $R^1$ is a methyl group; $R^2$ is a chlorine or bromine atom; $R^3$ is a hydrogen atom; A is an ethylene group; and $R^5$ is a phenyl group substituted at the 2-position with a methyl group and at the 4-position with an n-alkyl group having from 2 to 8 carbon atoms; and acid addition salts thereof.

17. The composition of claim 1 wherein in said compound of the formula (I), $R^4$ is a group $R^6$ which is one of said unsubstituted phenyl, substituted phenyl group, furyl and thienyl groups; and acid addition salts thereof.

18. The composition of claim 17 wherein in said compound of the formula (I), $R^1$ and $R^2$ are each selected from the group consisting of alkyl groups having from 1 to 4 carbon atoms and halogen atoms; $R^3$ is a hydrogen atom; A is an alkylene group having from 1 to 5 carbon atoms; and $R^6$ is selected from the group consisting of an unsubstituted phenyl group, a substituted phenyl group substituted with one or two substituents selected from the group consisting of halogen atoms, alkyl groups having from 1 to 5 carbon atoms, and alkoxy groups having from 1 to 4 carbon atoms, a furyl group and a thienyl group; and acid addition salts thereof.

19. The composition of claim 18 wherein in said compound of the formula (I), one of $R^1$ and $R^2$ is selected from the group consisting of chlorine and bromine atoms and the other is an alkyl group having from 1 to 4 carbon atoms; and acid addition salts thereof.

20. The composition of claim 17 wherein in said compound of the formula (I), A is a group of formula —CH($R^8$)— in which $R^8$ is an alkyl group having from 1 to 4 carbon atoms.

21. The composition of claim 20 wherein in said compound of the formula (I), $R^8$ is a methyl or ethyl group.

22. The composition of claim 18 wherein in said compound of the formula (I), $R^6$ is selected from the group consisting of an unsubstituted phenyl group and a substituted phenyl group substituted with one substituent selected from the group consisting of alkyl groups having from 1 to 4 carbon atoms, alkoxy groups having from 1 to 4 carbon atoms and halogen atoms; and acid addition salts thereof.

23. The composition of claim 22 wherein in said compound of the formula (I), $R^6$ is selected from the group consisting of an unsubstituted phenyl group and a substituted phenyl group substituted with one substituent selected from the group consisting of a methyl group, a methoxy group, a chlorine atom and a bromine atom; and acid addition salts thereof.

24. The composition of claim 18 wherein in said compound of the formula (I), $R^1$ is selected from the group consisting of a chlorine or bromine atom; $R^2$ is selected from the group consisting of a methyl and an ethyl group; $R^3$ is a hydrogen atom; A is selected from the group consisting of an ethylidene and a propylidene group; and $R^6$ is selected from the group consisting of a phenyl group and a phenyl group substituted with one methyl or methoxy group.

25. The composition of claim 1 wherein said compound of the formula (I) is 5-chloro-6-methyl-4-[2-(2-methyl-4-n-propylphenoxy)ethylamino]-pyrimidine.

26. The composition of claim 1 wherein said compound of the formula (I) is 4-[2-(4-n-butyl-2-methylphenoxy)ethylamino]-5-chloro-6-methyl-pyrimidine.

27. The composition of claim 1 wherein said compound of the formula (I) is 5-chloro-6-methyl-4-[2-(2-methyl-4-n-pentylphenoxy)ethylamino]-pyrimidine.

28. The composition of claim 1 wherein said compound of the formula (I) is 5-bromo-4-[2-(4-n-butyl-2-methylphenoxy)ethylamino]6-methyl-pyrimidine.

29. The composition of claim 1 wherein said compound of the formula (I) is 5-bromo-6-methyl-4-[2-(2-methyl-4-n-pentylphenoxy)ethylamino]-pyrimidine.

30. The composition of claim 1 wherein said compound of the formula (I) is 6-chloro-5-methyl-4-[1-methyl-2-(2-methylphenoxy)ethylamino]-pyrimidine.

31. The composition of claim 1 wherein said compound of the formula (I) is 5-chloro-6-methyl-4-[2-(2-methyl-4-n-pentylphenoxy)ethylamino]-pyrimidine hydrochloride.

32. The composition of claim 1 wherein said compound of the formula (I) is 5-chloro-4-[2-(2-chloro-6-methyl-4-n-propylphenoxy)ethylamino]-6-methylpyrimidine.

33. The composition of claim 1 wherein said compound of the formula (I) is 5-chloro-6-methyl-4-[2-(2,6-dimethyl-4-n-propylphenoxy)-ethylamino]-pyrimidine.

34. The composition of claim 1 wherein said compound of the formula (I) is 5-chloro-6-methyl-4-[2-(2-methyl-4-n-butylphenoxy)ethylamino]-pyrimidine nitrate.

35. The composition of claim 1 wherein said compound of the formula (I) is 5-chloro-6-methyl-4-[2-(2-methyl-4-allylphenoxy)ethylamino]-pyrimidine.

36. The composition of claim 1 wherein said compound of the formula (I) is 5-chloro-6-methyl-4-[2-(2- ethyl-4-n-pentylphenoxy)ethylamino]-pyrimidine nitrate.

37. A compound having the formula (I)

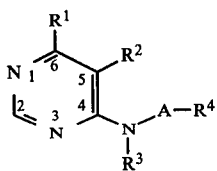

wherein
$R^1$ and $R^2$ are each methyl;
$R^3$ is selected from the group consisting of a hydrogen atom and alkyl groups having from 1 to 4 carbon atoms;
A is an alkylene group having 1 to 5 carbon atoms;
$R^4$ is the group $-OR^5$, and $R^5$ is selected from the group consisting of an unsubstituted phenyl group, and a substituted phenyl group substituted with one, two or three substituents selected from the group consisting of alkyl groups having from 1 to 10 carbon atoms, halogen atoms, alkoxy groups having from 1 to 4 carbon atoms, alkylthio groups having from 1 to 4 carbon atoms, alkenyl groups having from 3 to 4 carbon atoms, a trifluoromethyl group and a nitro group; and acid addition salts thereof.

38. A compound having the formula (I)

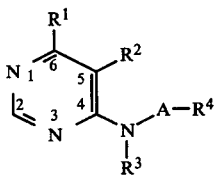

wherein
$R^1$ is an alkyl group having from 1 to 4 carbon atoms;
$R^2$ is chlorine or bromine;
A is an alkylene group having 1 to 5 carbon atoms;
$R^4$ is the group $-OR^5$, and $R^5$ is selected from the group consisting of an unsubstituted phenyl group, and a substituted phenyl group substituted with one, two or three substituents selected from the group consisting of alkyl groups having from 1 to 10 carbon atoms, halogen atoms, alkoxy groups having from 1 to 4 carbon atoms, alkylthio groups having from 1 to 4 carbon atoms, alkenyl groups having from 3 to 4 carbon atoms, a trifluoromethyl group and a nitro group; and acid addition salts thereof.

39. The compounds of claim 38 wherein $R^1$ is a methyl group.

40. The compounds of any of claims 37, 38 or 39 wherein $R^3$ is a hydrogen atom; A is an ethylene group; and $R^5$ is a phenyl group substituted at the 2-position with an alkyl group having from 1 to 4 carbon atoms; a phenyl group substituted at the 2-position with a methyl or ethyl and at the 4- or 5-position with an alkyl group having from 1 to 10 carbon atoms or with an allyl group; or a phenyl group substituted at the 2-position with a methyl group, at the 4-position with an alkyl group having from 1 to 10 carbon atoms and at the 6-position with a methyl group or a halogen atom; and acid addition salts thereof.

41. The compounds of claim 39, wherein $R^3$ is a hydrogen atom; A is an ethylene group; and $R^5$ is a phenyl group substituted at the 2-position with a methyl group and at the 4-position with an n-alkyl group having from 2 to 8 carbon atoms; and acid addition salts thereof.

42. The compound of claim 38 which is 5-chloro-6-methyl-4-[2-(2-methyl-4-n-propylphenoxy)ethylamino]-pyrimidine.

43. The compound of claim 38 which is 4-[2-(4-n-butyl-2-methylphenoxy)ethylamino]-5-chloro-6-methyl-pyrimidine.

44. The compound of claim 38 which is 5-chloro-6-methyl-4-[2-(2-methyl-4-n-pentylphenoxy)ethylamino]-pyrimidine.

45. The compound of claim 38 which is 5-bromo-4-[2-(4-n-butyl-2-methylphenoxy)ethylamino]-6-methyl-pyrimidine.

46. The compound of claim 38 which is 5-bromo-6-methyl-4-[2-(2-methyl-4-n-pentylphenoxy)ethylamino]-pyrimidine.

47. The compound of claim 38 which is 6-chloro-5-methyl-4-[1-methyl-2-(2-methylphenoxy)ethylamino]-pyrimidine.

48. The compound of claim 38 which is 5-chloro-6-methyl-4-[2-(2-methyl-4-n-pentylphenoxy)ethylamino]-pyrimidine hydrochloride.

49. The compound of claim 38 which is 5-chloro-4-[2-(2-chloro-6-methyl-4-n-propylphenoxy)ethylamino]-6-methylpyrimidine.

50. The compound of claim 38 which is 5-chloro-6-methyl-4-[2-(2,6-dimethyl-4-n-propylphenoxy)-ethylamino]-pyrimidine.

51. The compound of claim 38 which is 5-chloro-6-methyl-4-[2-(2-methyl-4-n-butylphenoxy)ethylamino]-pyrimidine nitrate.

52. The compound of claim 38 which is 5-chloro-6-methyl-4-[2-(2-methyl-4-allylphenoxy)ethylamino]-pyrimidine.

53. The compound of claim 38 which is 5-chloro-6-methyl-4-[2-(2-ethyl-4-n-pentylphenoxy)ethylamino]-pyrimidine nitrate.

* * * * *

UNITED STATES PATENT AND TRADEMARK OFFICE
CERTIFICATE OF CORRECTION

PATENT NO. : 4,435,402
DATED : March 6, 1984
INVENTOR(S) : Hideakira TSUJI et al It is certified that error appears in the above-identified patent and that said Letters Patent is hereby corrected as shown below:

Title Page: Replace the title with --FUNGICIDAL, INSECTICIDAL AND ACARICIDAL COMPOSITIONS CONTAINING AMINOPYRIMIDINE DERIVATIVES AND NOVEL AMINOPYRIMIDINE DERIVATIVES--.

Column 27, Table 1, 13th line from bottom of page: Replace the entire line with --286   4   315   3--.

Column 28, Table 2, 8th line from bottom of page: Replace the entire line with --107   4   189   4--.

Column 32, Table 7, last line, right-hand column: Replace "Z" with --2--.

Signed and Sealed this

Nineteenth Day of March 1985

[SEAL]

Attest:

DONALD J. QUIGG

Attesting Officer

Acting Commissioner of Patents and Trademarks